United States Patent
Liang et al.

(10) Patent No.: US 10,695,355 B2
(45) Date of Patent: Jun. 30, 2020

(54) METHODS FOR PHARMACOLOGIC TREATMENT OF STROKE

(71) Applicants: University of Connecticut, Farmington, CT (US); The United States of America, as represented by the Secretary, Department of Health and Human Services, Bethesda, ME (US)

(72) Inventors: Bruce Liang, Avon, CT (US); Rajkumar Verma, New Haven, CT (US); Kenneth A. Jacobson, Silver Spring, MD (US)

(73) Assignees: UNIVERSITY OF CONNECTICUT, Farmington, CT (US); THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 90 days.

(21) Appl. No.: 15/933,536

(22) Filed: Mar. 23, 2018

(65) Prior Publication Data
US 2018/0280409 A1 Oct. 4, 2018

Related U.S. Application Data

(60) Provisional application No. 62/478,655, filed on Mar. 30, 2017.

(51) Int. Cl.
| | |
|---|---|
| *A61K 31/5513* | (2006.01) |
| *A61P 9/10* | (2006.01) |
| *A61K 9/00* | (2006.01) |
| *A61K 47/38* | (2006.01) |
| *A61K 47/20* | (2006.01) |
| *A61K 31/551* | (2006.01) |
| *A61K 31/5517* | (2006.01) |

(52) U.S. Cl.
CPC ........ *A61K 31/5513* (2013.01); *A61K 9/0019* (2013.01); *A61K 9/0053* (2013.01); *A61K 47/20* (2013.01); *A61K 47/38* (2013.01); *A61P 9/10* (2018.01); *A61K 31/551* (2013.01); *A61K 31/5517* (2013.01)

(58) Field of Classification Search
CPC .............. A61K 31/551; A61K 31/5513; A61K 31/5517
USPC ....................................................... 514/220
See application file for complete search history.

(56) References Cited

U.S. PATENT DOCUMENTS 8,470,814 B2 * 6/2013 Sakuma ............... C07D 403/10
514/220
2013/0281441 A1 10/2013 Sakuma et al.

FOREIGN PATENT DOCUMENTS

WO 2004085440 A1 10/2004

OTHER PUBLICATIONS

O'Donnell et al., "Chronic Pain Syndromes After Ischemic Stroke PRoFESS Trial", Stroke, vol. 44. No. 5, pp. 1238-1247 (2013).*
Balazs et al.; "Investigation of the Inhibitory Effects of the Benzodiazepine Derivative, 5-BDBD on P2X4 Purinergic Receptors by Two Complementary Methods"; Cellular Physiology and Biochemistry; 32; pp. 11-24; (2013).
Chen et al.; "Electroacupuncture Inhibits Excessive Interferon-Y Evoked Up-Regulation of P2X4 Receptor in Spinal Microglia in a CCI Rat Model for Neuropathic Pain"; British Journal of Anaesthesia; 114(1); pp. 150-157; (2015).
Cioffi, Christopher L.; "Modulation of Glycine-Mediated Spinal Neurotransmission for the Treatment of Chronic Pain"; Journal of Medicinal Chemistry; 61; pp. 2652-2679; (2018).
Hernandez-Olmos et al.; "N-Substituted Phenoxazine and Acridone Derivatives: Structure-Activity Relationships of Potent P2X4 Receptor Antagonists"; Journal of Medicinal Chemistry; 55(22); pp. 9576-9588; (2012).
Jacobson et al.; "Ocular Purine Receptors as Drug Targets in the Eye"; Journal of Ocular Pharmacology and Therapeutics; 32(8); pp. 534-547; (2016).
Layhadi et al.; "P2X4 Receptor-Dependent Ca2+ Influx in Model Human Monocytes and Macrophages"; Internal Journal of Molecular Sciences; 18; pp. 2261; 13 pages; (2017).
Macedo, Jr. et al.; "The Involvement of Purinergic System in Pain: Adenosine Receptors and Inosine as Pharmacological Tools in Future Treatments"; in Pharmacology, Dr. Luca Gallelli, Editor; Publisher INTECH; Published online Mar. 14, 2012); pp. 627-651; (2012).
Matsumura et al.; "A Novel P2X4 Receptor-selective Antagonist Produces Anti-allodynic Effect in a Mouse Model of Herpetic Pain"; Scientific Reports; 6:32461; 11 pages; (2016).
Poster; Rajkumar Verma et al;"P2X4 Receptor Ablation Reduces Infarct Size Acutely but is Associated with Depression Like Behaviou Chronically"; Presented at International Brain Injury Association's 12th World Congress on Brain Injury; Mar. 29 to Apr. 1, 2017, New Orleans, Louisiana; Accepted Abstract from (2017) Accepted Abstracts from the International Brain Injury Association's 12th World Congress on Brain Injury, Brain Injury, 31:6-7, 719-1017, DOI: 10.1080/02699052.2017.1312145.
TOCRIS Data Sheet for BX 430, CAS 688309-70-8; 2 pages; Printed Oct. 8, 2015.

(Continued)

*Primary Examiner* — Kevin E Weddington
(74) *Attorney, Agent, or Firm* — Cantor Colburn LLP

(57) ABSTRACT

Described herein are methods for the treatment of a human subject who has had a stroke by administering to the subject a pharmaceutical composition including an antagonist of the P2X4 receptor. The antagonist of the P2X4 receptor can be administered in the acute phase of stroke, optionally in combination with a thrombolytic therapeutic or a procedure on the subject involving a clot-removal device.

14 Claims, 11 Drawing Sheets
(5 of 11 Drawing Sheet(s) Filed in Color)

(56) References Cited

OTHER PUBLICATIONS

Tsuda et al.; "P2X4 Receptors Induced in Spinal Microglia Gate Tactile Allodynia After Nerve Injury"; Letters to Nature; Nature; 424; pp. 778-783; (2003).

Ulmann et al.; "P2X4 Receptors Mediate PGE2 Release by Tissue-Resident Macrophages and Initiate Inflammatory Pain"; The EMBO Journal; 29; pp. 2290-2300; (2010).

Wang et al.; Abstract 132 Synthesis of PSB-12054 and its Analogs as New Potential P2X4 Receptor Antagonists; Scientific Abstracts for the 255th National Meeting and Exposition; Mar. 18-22, 2018, New Orleans, LA; 2 pages.

Wixey et al.; Delayed P2X4R Expression After Hypoxia-Ischemia is Associated With Microglia in the Immature Rat Brain; Journal of Neuroimmunology; 212; pp. 35-43; (2009).

Verma et al.; "Deletion of the P2X4 Receptor is Neuroprotective Acutely, but Induces a Depressive Phenotype During Recovery From Ischemic Stroke"; Brain, Behavior, and Immunity; 66; pp. 302-312; (2017).

\* cited by examiner

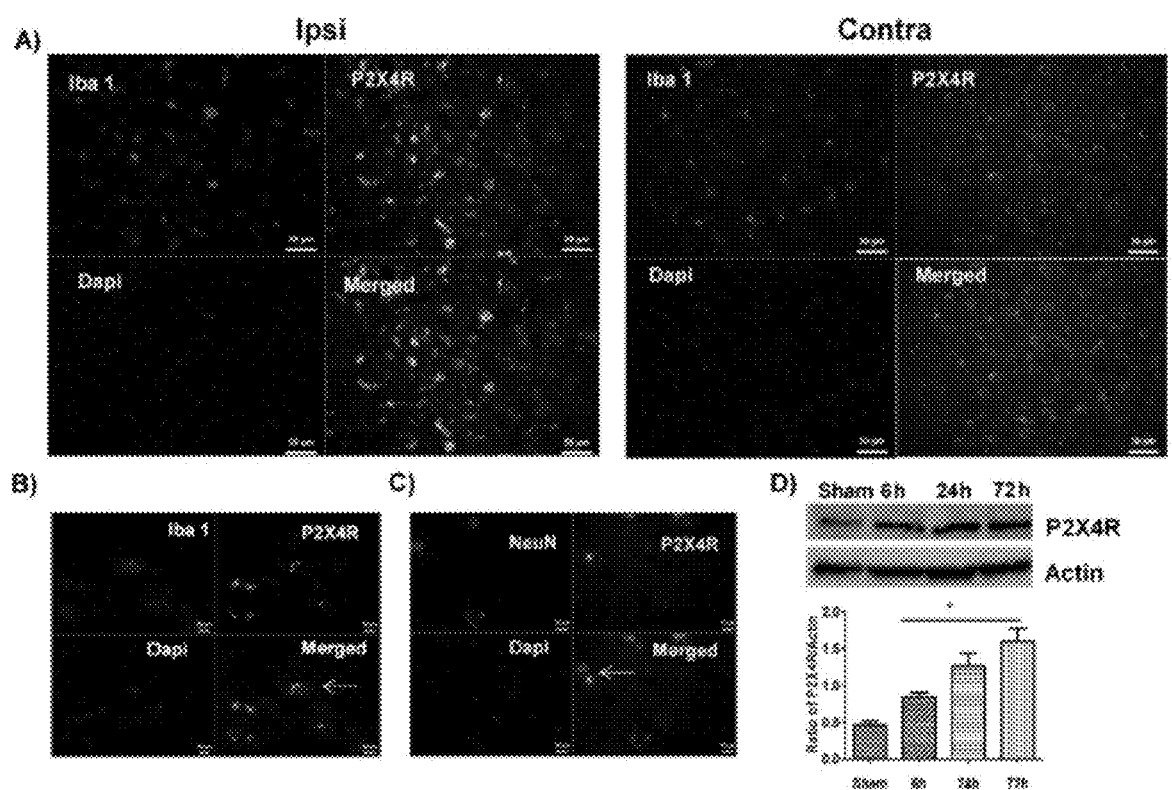
FIG. 1A-D

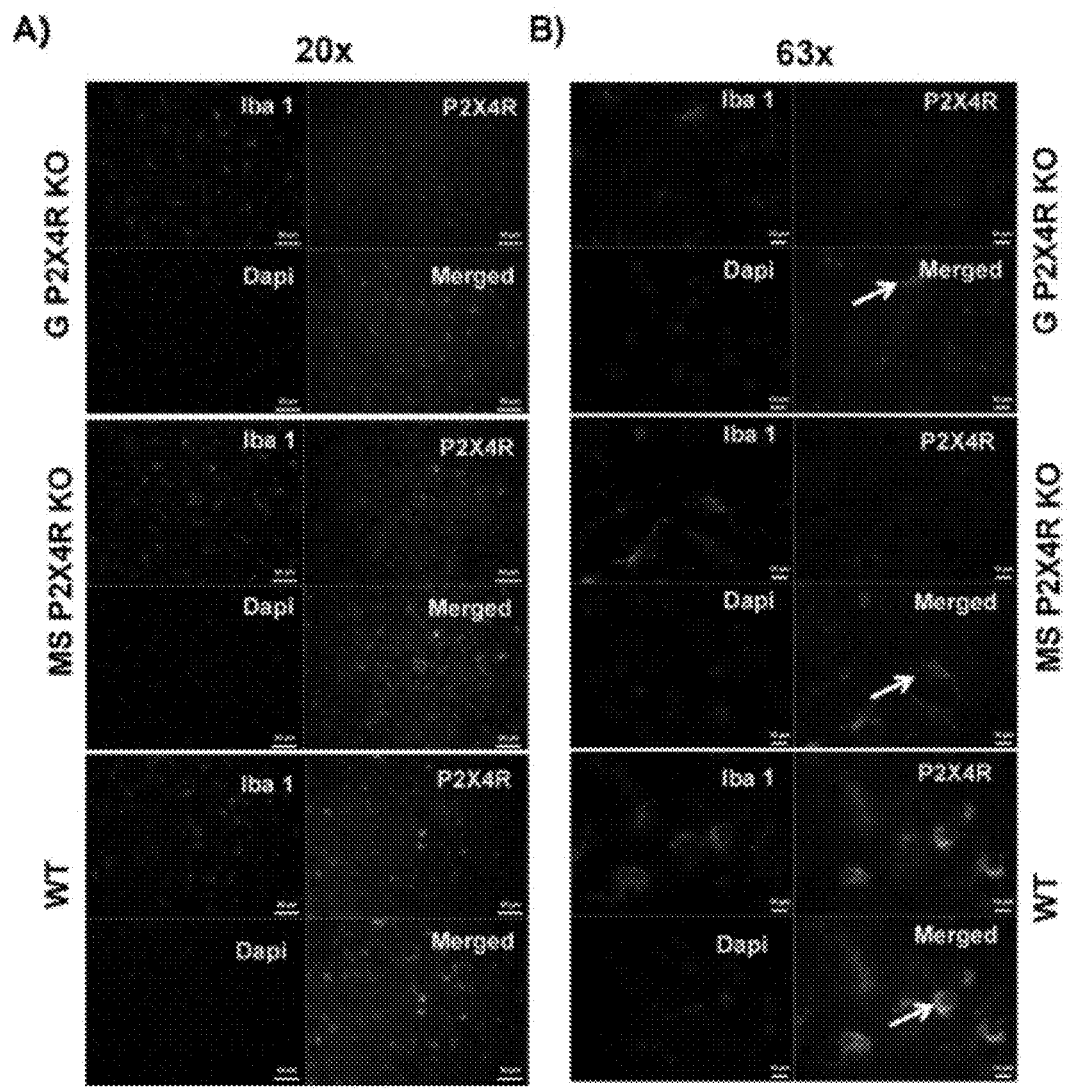
FIG. 2A and B

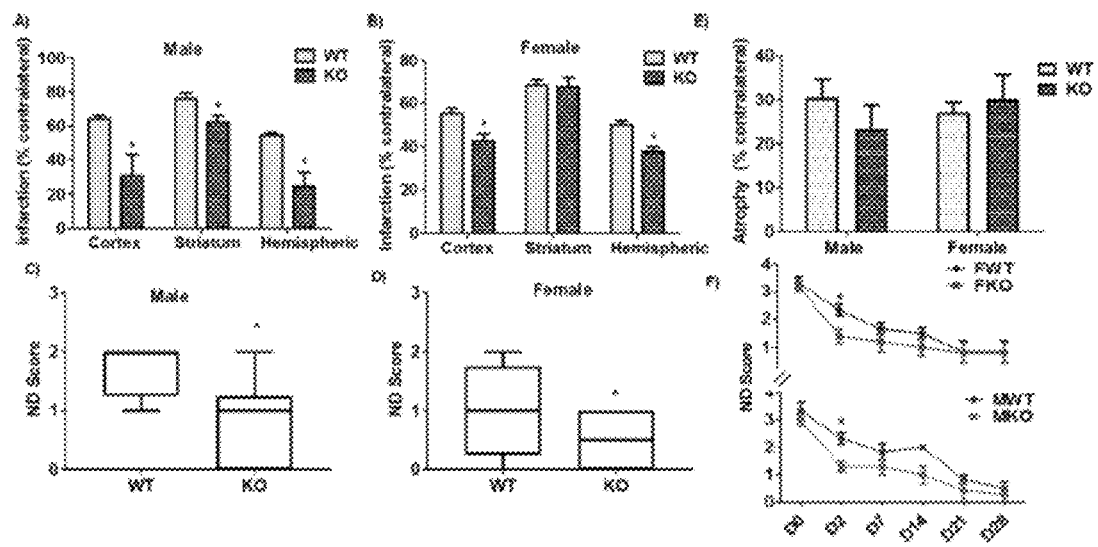
FIG. 3A-F
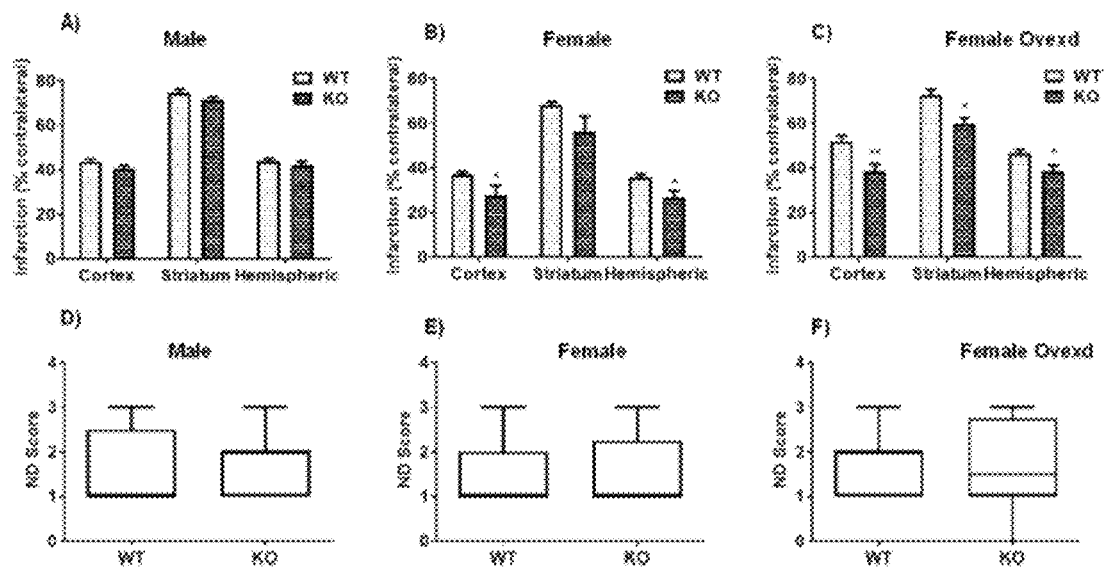
FIG. 4A-F

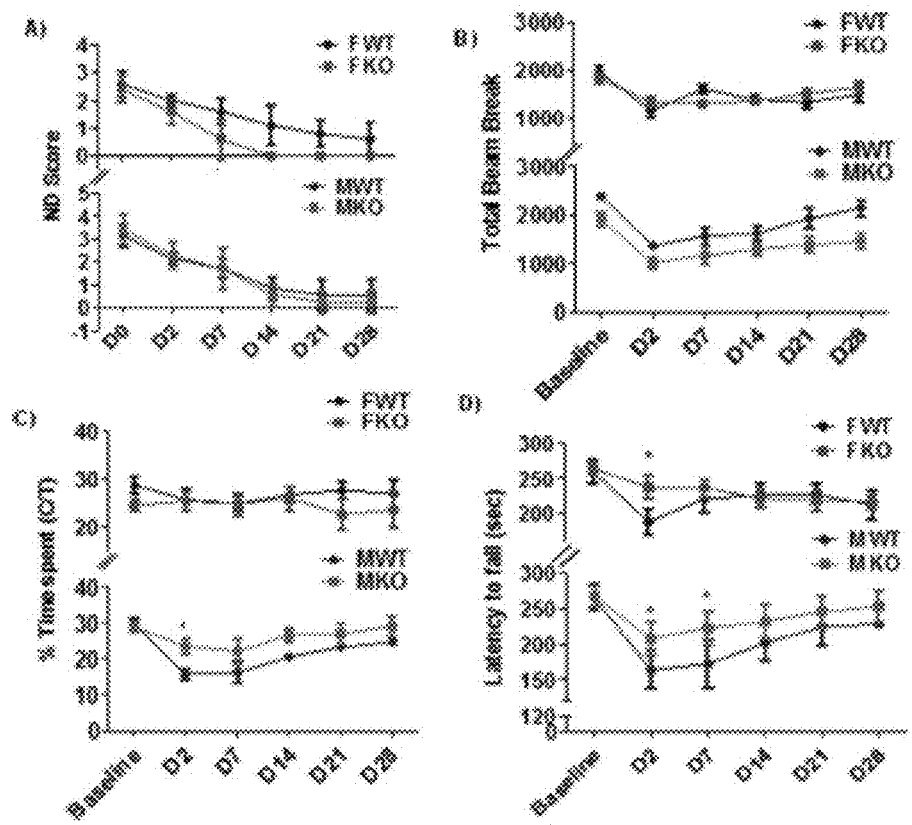
FIG. 5A-D
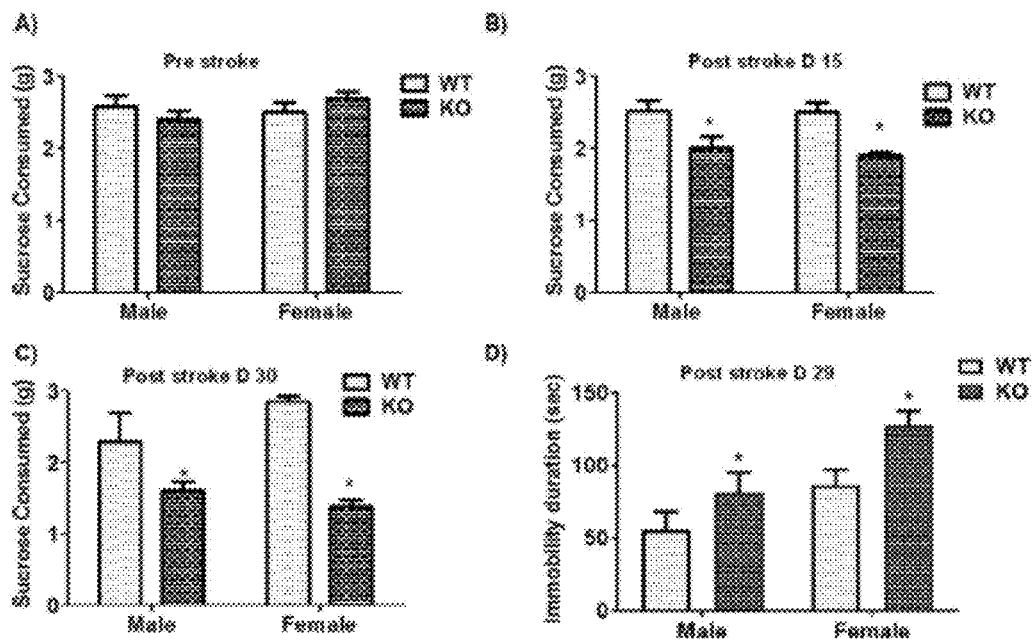
FIG. 6A-D

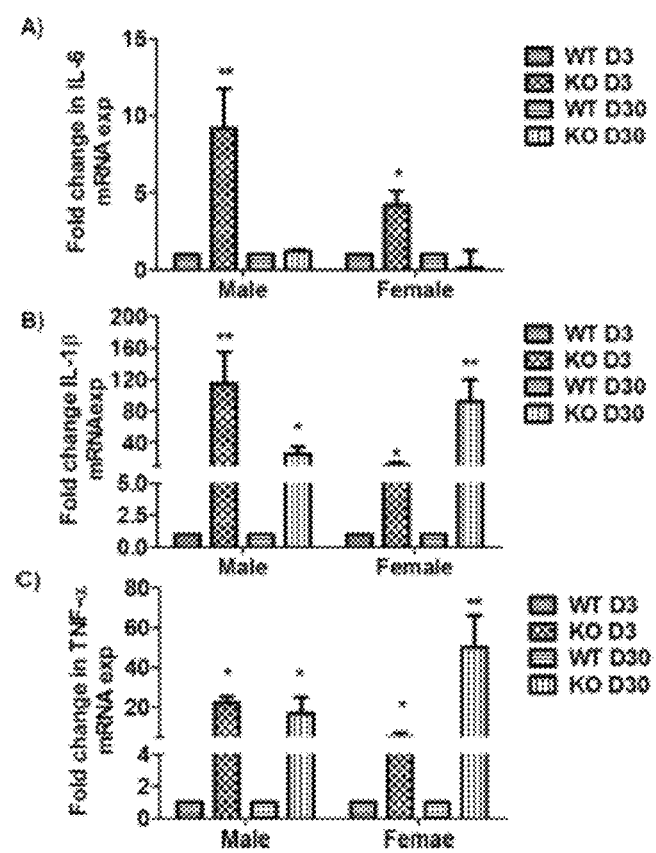
FIG. 7A-C

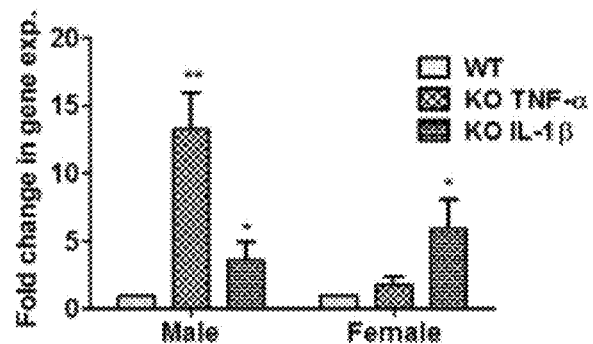
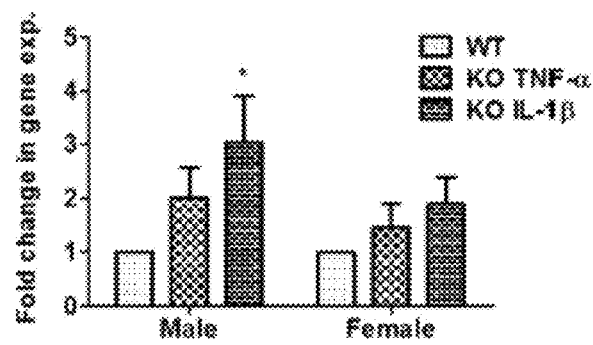
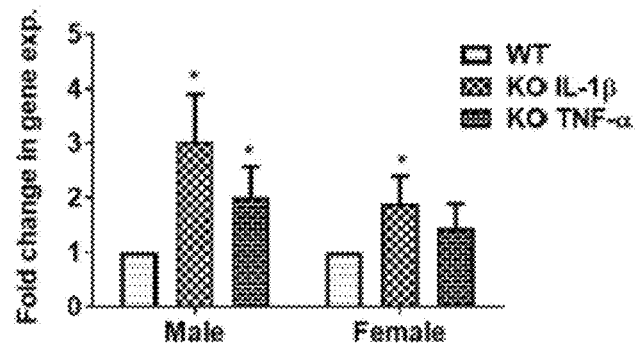
FIG. 8A-C
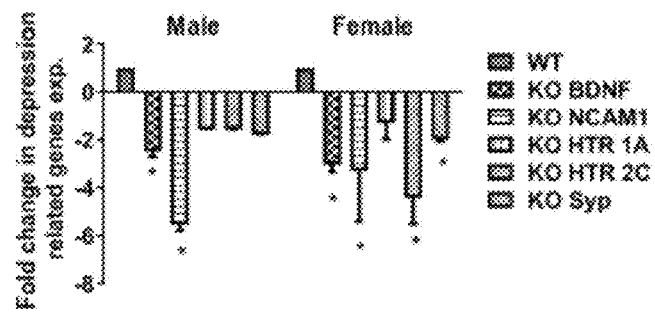
FIG. 9

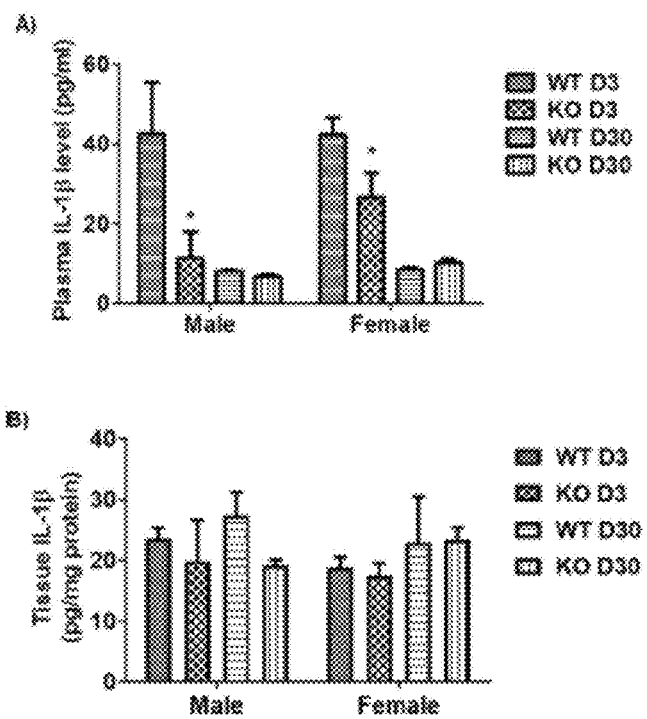
FIG. 10A and B
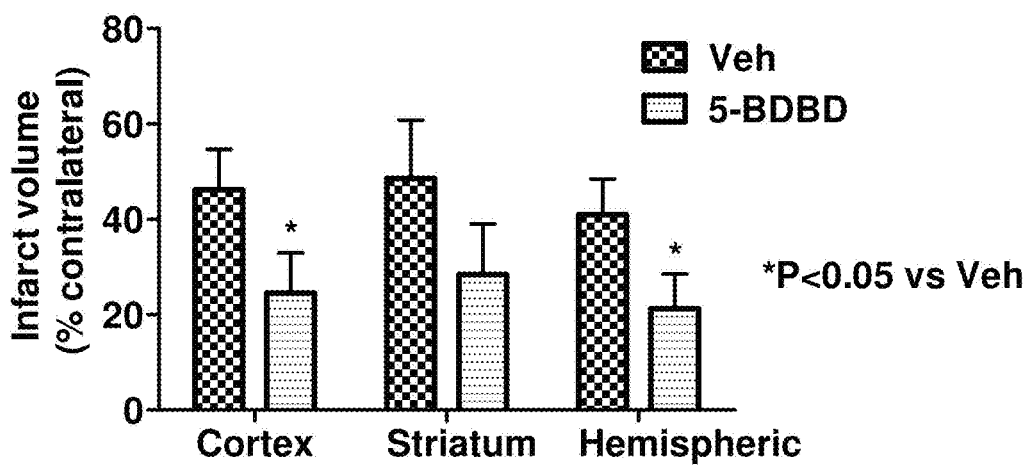
FIG. 11

METHODS FOR PHARMACOLOGIC TREATMENT OF STROKE

CROSS-REFERENCE TO RELATED APPLICATIONS

This application claims priority to U.S. Provisional Application Ser. No. 62/478,655 filed on Mar. 30, 2017, which is incorporated herein by reference in its entirety.

FIELD OF THE DISCLOSURE

The present disclosure is related to methods for the treatment of stroke, specifically ischemic stroke.

BACKGROUND

Stroke is the fifth leading cause of death for Americans and a leading cause of serious long-term disability. Every year, more than 795,000 people in the United States have a stroke. Stroke kills more than 130,000 Americans each year, which is about 1 out of every 20 deaths. About 87% of all strokes are ischemic strokes, in which the blood flow to the brain is blocked. Stroke costs the United States an estimated $33 billion each year. This total includes the cost of health care services, medicines to treat stroke, and missed days of work.

Current approaches to treating ischemic stroke are primarily limited to the administration of thrombolytic therapeutics such as tissue plasminogen activator, or to an invasive endovascular procedure involving the use of a clot removing/retrieving device. Thrombolytic therapeutics, however, must be given during the first few hours of a stroke, are associated with a risk of bleeding, and are only useful for ischemic strokes, not for hemorrhagic strokes. The clot removing/retrieving device is applicable in less than 10% of embolic stroke cases. Thus, improved medical therapy for stroke, particularly ischemic stroke, is needed and represents an unmet area of need.

BRIEF SUMMARY

In an aspect, a method for treatment of a human subject who has had a stroke comprises administering to the subject a pharmaceutical composition comprising an antagonist of the P2X4 receptor.

In an aspect, the antagonist of the P2X4 receptor is a compound of Formula (I)

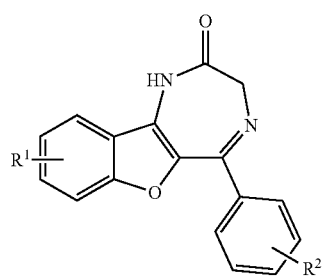

(I)

wherein $R^1$ is hydrogen, halogen, $C_1$-$C_6$ alkyl, $C_1$-$C_6$ haloalkyl, $C_1$-$C_6$ alkoxy, $C_1$-$C_6$ haloalkoxy, nitro, cyano, aryl, heteroaryl, heterocycloalkyl, $C_2$-$C_6$ alkanoyl, —COOH, —$NR^4R^5$, —C(O)—$OR^3$, —C(O)—$NR^4R^5$, —$SO_2$—$OR^5$ or —$SO_2$—$NR^4R^5$, wherein $R^3$, $R^4$, and $R^5$ are independently hydrogen or $C_1$-$C_6$ alkyl; and $R^2$ is hydrogen, halogen, $C_1$-$C_6$ alkyl, $C_1$-$C_6$ haloalkyl, $C_1$-$C_6$ alkoxy, $C_1$-$C_6$ haloalkoxy, nitro, cyano, aryl, heteroaryl, heterocycloalkyl, $C_2$-$C_6$ alkanoyl, —COOH, —$NR^4R^5$, —C(O)—$OR^3$, —C(O)—$NR^4R^5$, —$SO_2$—$OR^5$ or —$SO_2$—$NR^4R^5$, wherein $R^3$, $R^4$, and $R^5$ are independently hydrogen or $C_1$-$C_6$ alkyl; or a pharmaceutically acceptable salt thereof.

In another aspect, the antagonist of the P2X4 receptor is a compound of Formula (II)

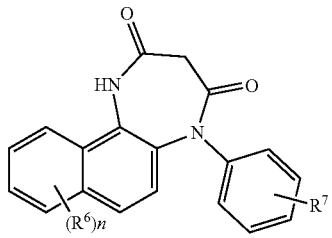

(II)

wherein $R^6$ is hydrogen, halogen, $C_1$-$C_6$ alkyl, $C_1$-$C_6$ haloalkyl, $C_1$-$C_6$ alkoxy, $C_1$-$C_6$ haloalkoxy, nitro, cyano, aryl, heteroaryl, heterocycloalkyl, $C_2$-$C_6$ alkanoyl, —COOH, —$NR^4R^5$, —C(O)—$OR^3$, —C(O)—$NR^4R^5$, —$SO_2$—$OR^5$ or —$SO_2$—$NR^4R^5$, wherein $R^3$, $R^4$, and $R^5$ are independently hydrogen or $C_1$-$C_6$ alkyl;

n is 0, 1, 2, or 3;

$R^7$ is halogen, $C_1$-$C_6$ alkyl, $C_1$-$C_6$ haloalkyl, $C_1$-$C_6$ alkoxy, $C_1$-$C_6$ haloalkoxy, nitro, cyano, aryl, heteroaryl, heterocycloalkyl, $C_2$-$C_6$ alkanoyl, —COOH, —$NR^4R^5$, —C(O)—$OR^3$, —C(O)—$NR^4R^5$, —$SO_2$—$OR^5$ or —$SO_2$—$NR^4R^5$, wherein $R^3$, $R^4$, and $R^5$ are independently hydrogen or $C_1$-$C_6$ alkyl; or a pharmaceutically acceptable salt thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-D show immunolabeling of P2X4R in male WT mice three days after stroke induction. FIG. 1A shows P2X4R expression (green) was increased and Iba 1+ cells (red) showed an activated phenotype (round cell bodies with low processes) in the ipsilateral (stroke) versus contralateral (non-stroke) hemisphere (20×; scale bar 50 μm). FIG. 1B shows ipsilateral staining: P2X4R (green) co-localized with Iba+ cells (red) (63×; scale bar 10 μm). FIG. 1C shows ipsilateral staining: Co-localization of P2X4R (green) with $NeuN^{+ve}$ neurons (red) and DAPI (blue; marking nuclei) showed qualitatively reduced expression of P2X4R in neurons (n=3 M WT) (63×; scale bar 10 μm). FIG. 1D shows stroke led to a significant time-dependent increase in P2X4R expression in whole cell lysate from the ipsilateral brain (*p<0.05; stroke vs. sham, one-way-ANOVA; graphs show mean+S.E.M.; n=12; 3/group/time point; no exclusion).

FIGS. 2A and B show qualitative microglia activation phenotype after three days of stroke in the perilesional cortex of the ipsilateral hemisphere on (FIG. 2A) lower magnification (20×; scale bar 50 μm) and (FIG. 2B) higher magnification (63×; scale bar 10 μm). We examined Iba-1 and P2X4R co-immunostained microglia. Global and MS P2X4R KO mice showed intermediate activation of microglia, based on shorter processes, less arborization, and larger soma. WT mice showed an amoeboid or round morphology characteristic of a highly activated state.

FIGS. 3A-F show the effect of stroke on infarct volume and ND score in global P2X4R KO mice. FIG. 3A shows the volume was significantly reduced ($p<0.05$ vs. WT littermate, two-tailed Student's t-test, n, KO=6 WT=9) in cortical, striatal, and total hemispheric infarct in global KO male mice. FIG. 3B shows female global KO mice displayed a similar reduction in the volume of cortical and total hemispheric infarct ($p<0.05$; KO vs. WT littermates, two-tailed Student's t-test; KO=6, WT=8) but not in the striatum. FIG. 3C and FIG. 3D shows ND scores which confirmed acute behavioral benefits in both sexes as compared to WT controls (*$p<0.05$; KO vs. WT; Mann-Whitney U test). We did not observe a change in (FIG. 3E) tissue atrophy or (FIG. 3F) ND score between global KO and WT mice for males (M) or females (FIG. 3F) at a chronic stage of stroke (day 30). However, a two-way ANOVA (genotype vs time) analysis in male [$F_{(1, 66)}=16.07$; $p=0.002$)] as well as female [$F_{(1, 54)}=3.927$; $p=0.05$] suggested a main effect of genotype (KO=6 and WT=8). Further, a multiple comparison analysis at individual time point between KO and WT of both sexes showed a significant difference in ND score at day 2 after stroke (*$p<0.05$ vs. WT; Mann-Whitney-U test;) (FWT—female WT, KO—Female KO; MWT—male WT, MKO—male WT).

FIGS. 4A-F show the effect of stroke on infarct volume and ND score in MS P2X4R KO mice. FIG. 4A shows male mice did have any differences in infarct volume or ND score between KO (n=7) and WT (n=9) mice after three days of stroke. FIG. 4B shows female mice had a significant reduction in cortical and total hemispheric (but not striatal) infarct volume between KO (n=6) and WT (n=10) mice at an equivalent time point (*$p<0.05$; KO vs. WT littermates; two-tailed Student's t-test; graphs showed mean±S.E.M.) but did not show any change in ND score (one mouse was excluded due to death). FIG. 4C shows the same magnitude of difference in infarct volume was maintained in ovxed female KO (n=18) and WT (n=11) mice (**$p<0.01$, *$p<0.05$ vs. WT littermates, two-tailed Student's t-test, graphs showed mean±S.E.M), suggesting no effect of ovarian hormone estrogen for neuroprotection in female KO mice after stroke. FIG. 4D and FIG. 4F show that moreover, similar to non-ovxed mice, ovxed KO and WT females did not show any difference in ND score (Mann-Whitney U test).

FIGS. 5A-D show the effect of stroke on sensorimotor deficits in male (M) and female (F) MS P2X4R KO mice. FIG. 5A shows that we did not observe a difference in ND Score between KO (n=7) and WT (n=10) male mice [$F_{(1, 66)}=0.3$, $p=0.5858$; two-way ANOVA). Female KO (n=8) versus WT (n=9) mice recovered completely (based on ND score) within two weeks. A two-way ANOVA suggested a significant main effect of genotype in female [$F_{(1, 78)}=47.76$; $p<0.0001$ WT vs KO]. FIG. 5B shows that we observed no differences between genotype in total exploratory activity measured by the OFT after baseline correction in either male or female. FIG. 5C shows male KO mice showed as a swift reversal of anxiety-like behavior during the first week of stroke where a two-way ANOVA suggested a significant main effect of genotype ($F_{(1, 66)}=14.48$; $p=0.0003$] and multiple comparison analysis at different time points suggested a significant difference at day 2 (*$p<0.05$; KO vs. WT;); we observed no differences in females. FIG. 5D shows that in the rotarod test, both male and female KO mice showed reduced impact of ischemic injury on motor balance and coordination during the acute recovery period (days 2-7 post stroke). In male mice a two-way ANOVA suggested a significant main effect of genotype [($F_{(1, 66)}=4.51$; $p=0.034$)]. However in female a two-way ANOVA did not show a significant main effect of genotype [$F_{(1, 78)}=1.19$ $p=0.2786$). However, multiple time point comparison test suggested a significant effect at day 2 in both sexes (*$p<0.05$; KO vs. WT). A total of six mice died before the completion of experiments and were not included in the analysis.

FIGS. 6A-D show the effect of stroke on depressive-like behaviors in MS P2X4R KO mice. FIG. 6A shows at baseline, both male and female mice showed no difference in the consumption of sucrose. However, MS P2X4R KO mice showed reduced consumption of sucrose pellet at post-stroke (FIG. 6B) day 15 [male (KO=10, WT=7) and female (KO=8, WT=9)] and (FIG. 6C) day 30 [males (KO=5, WT=4) and females (KO=3, WT=4)]. FIG. 6D shows consistent with the SCT data, these mice (both sexes) [Female KO=8 WT=9; Male KO=7, WT=10)] showed a significant increase in depressive behavior (immobility duration) measured by the TST after 29 days of stroke (*$p<0.05$; KO vs. WT; two-tailed Student's t-test).

FIGS. 7A-C show a qPCR analysis of mRNA isolated from the perilesional ipsilateral cortex of MS P2X4R KO and WT mice. KO mice (n=3-4 mice/sex/group/time point; total of 26 mice) showed significant upregulation of the pro-inflammatory cytokines (FIG. 7A) IL-6, (FIG. 7B) IL-1β, and (FIG. 7C) TNF-α at both acute and chronic time points, with the exception of IL-6 levels, which did not change for either sex at the chronic time point of recovery. Data are expressed as mean±SEM and values on the Y axis are presented as fold change in gene expression of KO mice against their respective WT control, whose value were kept constant at 1 in determining fold change in KO (**$p<0.01$, *$p<0.05$; KO vs. WT, two-tailed Student's t-test).

FIGS. 8A-C show mRNA expression analysis of the pro-inflammatory cytokines TNF-α and IL-1β in flow-sorted microglia and monocyte after stroke in MSP2X4R KO and WT mice. FIG. 8A shows microglia sorted at day 3 [males (KO=5, WT=4) and females (KO=4, WT=5); total of 18 mice] showed significantly higher levels of TNF-α in males (**$p<0.01$; KO vs. WT, two-tailed Student's t-test) and a trend of elevation in females. IL-1β levels were elevated in both sexes (*$p<0.05$; KO vs. WT two-tailed Student's t-test). FIG. 8B shows an mRNA analysis from microglia sorted after 30 days showed elevated levels of IL-1β in males (*$p<0.01$; KO vs. WT, two-tailed Student's t-test) and a trend of elevation in females. No change in TNF-α was found for either of sex (n=3 mice/group/sex; total 12). FIG. 8C shows monocytes sorted at day 3 after stroke showed elevated levels of both IL-1β in both sexes (*$p<0.05$; KO vs. WT; two-tailed Student's t-test). TNF-α increased in male (*$p<0.05$; KO vs. WT; two-tailed Student's t-test) and showed a trend for increase in female KO. Very few monocytes were detected in the brain after 30 days, so no detectable expression of either gene was found. Similarly, no IL-6 levels exceeded the detection limit in both sorted microglia and monocytes. Data were expressed as mean±SEM and values on the Y axis were plotted as fold change in gene expression of KO mice against their respective WT control.

FIG. 9 shows a qPCR analysis of depression-related genes. Several genes (BDNF, NCAM1, HTR 1a, HTR 2c and Syp) implicated in depression were downregulated in MS P2X4R KO in both male and female mice chronically after stroke (day 30). Data are expressed as mean±SEM and values on the Y axis are presented as fold change in gene expression of KO mice against their respective WT control (*p<0.05; KO vs. WT; two-tailed Student's t-test).

FIGS. 10 A and B show IL-1β plasma and brain tissue protein levels examined using ELISA. FIG. 10A shows IL-1β plasma levels were significantly reduced in KO mice at an acute time point (day 3) following stroke in both sexes (*p<0.05; KO vs. WT; two-tailed Student's t-test), but no change was seen at a chronic time point (day 30). FIG. 10B shows tissue protein levels were not different between KO and WT mice at any time point after stroke in both sexes. Data were expressed as mean±SEM and were plotted as IL-1β pg/ml plasma (A) or mg/tissue protein.

FIG. 11 shows 5-BDBD post treatment reduces cortical and hemispheric infarct volume after 3 days of stroke.

Figure 12:
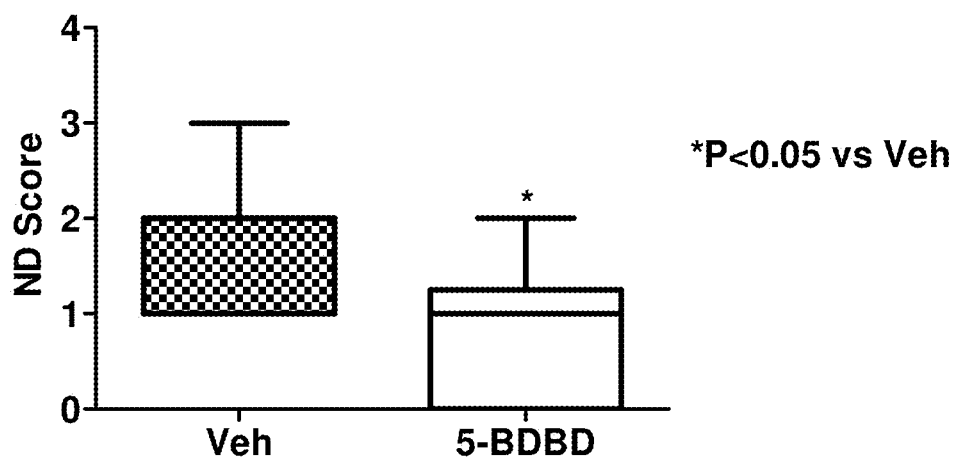
FIG. 12 shows 5-BDBD reduces Neurological deficit score measured after 3 days of stroke.

The above-described and other features will be appreciated and understood by those skilled in the art from the following detailed description, drawings, and appended claims.

DETAILED DESCRIPTION

Disclosed herein are methods of using P2X4 receptor antagonists as a new approach for treating ischemic stroke. Such methods may be used as an adjunct therapy concomitant with thrombolytic therapeutics and/or clot retrieval. In other situations, the P2X4 receptor antagonists may be used without concomitant use of thrombolytic therapeutics and/or clot retrieval.

The P2X4 receptor (P2X4R), a purinergic, ATP-activated ion channel receptor, is an important neurotransmitter receptor in the brain. These receptors are highly expressed in all cell types of the central nervous system (CNS) including neuronal cells, but are especially abundant on myeloid origin cells of the brain such as microglia. Microglia, the resident immune cells of the CNS, respond to disruptions in homeostasis in brain function and become activated. It is known that excessive release of ATP occurs from dying cells during stroke, resulting in activation of membrane-bound P2X4Rs in both microglia and post synaptic neurons, however, the role of P2X4R in the pathophysiology of stroke is not well understood. P2X4R mediated excessive influx of calcium leads to inflammasome activation and excitotoxic cell death in the neurons of the affected brain region. Extracellular ATP-binding to the microglial P2X4R receptor increases microglial proliferation and secretion of pro-inflammatory cytokines such as IL-1β, TNF-α. On the other hand, these receptors also mediate BDNF release from microglia, and BDNF is an essential neurotrophin in maintaining synaptic plasticity and cognition that are key for post-stroke recovery.

The data provided herein support that global absence of P2X4R provides early neuroprotection following stroke. However, when the inventors deleted P2X4R specifically in myeloid cells, only female mice showed acute neuroprotection, independent of estrogen levels. Both male and female MS P2X4R KO mice showed increased mRNA levels for cellular pro-inflammatory cytokines, but reduced levels of corresponding mature cytokines in plasma. Furthermore, both male and female MS P2X4R KO mice showed depressive-like behaviors, which is, to the inventors' knowledge, the first link between depression and P2X4R in myeloid cells. The depressive-like behavior in the MS P2X4R KO mice might be due to a P2X4R-mediated microglial response. Preliminary findings suggest an interference in cytokine release/signaling and a reduction in BDNF levels and serotonergic signaling in these KO animals. In sum, the inventors' study indicates that P2X4R-based pharmacotherapy should be undertaken in a time-sensitive manner after stroke. Acute inhibition of the receptor is expected to provide a benefit whereas chronic blockade might further exacerbate depressive behaviors.

More specifically, disclosed herein is a method of administering P2X4 receptor antagonists during the acute phase of stroke recovery (from a few hours after stroke to about 7 days after stroke) to achieve an improved functional outcome. The data described here summarize the effect on neurological deficit (ND) score from oral administration of the P2×4 blocker 5-BDBD [5-(3-Bromophenyl)-1,3-dihydro-2H-Benzofuro[3,2-e]-1,4-diazepin-2-one] at 0.5 mg/kg daily for 5 days beginning on the day of stroke induced by middle cerebral artery occlusion (60 minute) followed by reperfusion. The ND score improved significantly after 5 daily doses. The data are consistent with a beneficial effect on stroke infarct size and ND score in mice with knockout of P2X4 receptors.

In an aspect, a method for treatment of a human subject who has had a stroke comprises administering to the subject a pharmaceutical composition comprising an antagonist of a P2X4 receptor. In an aspect, an antagonist of the P2X4 receptor has an $IC_{50}$ of about 10-50 nM to about 500 to 1,000 nM, a negligible effect as an antagonist of P2X receptors other than P2X4, or a combination thereof.

In an embodiment, the antagonist of a P2X4 receptor comprises a compound of Formula (I)

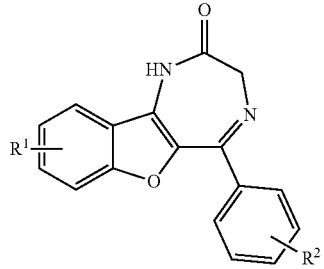
(I)

wherein $R^1$ is hydrogen, halogen, $C_1$-$C_6$ alkyl, $C_1$-$C_6$ haloalkyl, $C_1$-$C_6$ alkoxy, $C_1$-$C_6$ haloalkoxy, nitro, cyano, aryl, heteroaryl, heterocycloalkyl, $C_2$-$C_6$ alkanoyl, —COOH, —$NR^4R^5$, —C(O)—$OR^3$, —C(O)—$NR^4R^5$, —$SO_2$—$OR^5$ or —$SO_2$—$NR^4R^5$, wherein $R^3$, $R^4$, and $R^5$ are independently hydrogen or $C_1$-$C_6$ alkyl; and $R^2$ is hydrogen, halogen, $C_1$-$C_6$ alkyl, $C_1$-$C_6$ haloalkyl, $C_1$-$C_6$ alkoxy, $C_1$-$C_6$ haloalkoxy, nitro, cyano, aryl, heteroaryl, heterocycloalkyl, $C_2$-$C_6$ alkanoyl, —COOH, —$NR^4R^5$, —C(O)—$OR^3$, —C(O)—$NR^4R^5$, —$SO_2$—$OR^5$ or —$SO_2$—$NR^4R^5$, wherein $R^3$, $R^4$, and $R^5$ are independently hydrogen or $C_1$-$C_6$ alkyl; and pharmaceutically acceptable salts thereof.

In an embodiment, the compound of formula (I) has Formula (Ia), wherein $R^1$ and $R^2$ are as defined above.

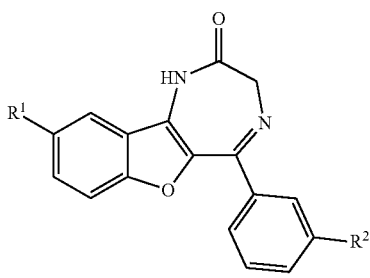
(Ia)

In an embodiment, the compound of Formula (I) is 5-BDBD [5-(3-Bromophenyl)-1,3-dihydro-2H-Benzofuro[3,2-e]-1,4-diazepin-2-one], or a pharmaceutically acceptable salt thereof.

In another embodiment, the antagonist of the P2X4 receptor is a compound of Formula (II)

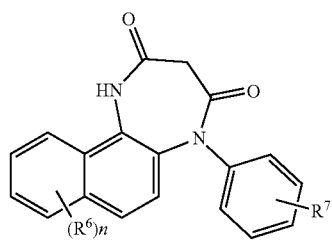
(II)

wherein $R^6$ is hydrogen, halogen, $C_1$-$C_6$ alkyl, $C_1$-$C_6$ haloalkyl, $C_1$-$C_6$ alkoxy, $C_1$-$C_6$ haloalkoxy, nitro, cyano, aryl, heteroaryl, heterocycloalkyl, $C_2$-$C_6$ alkanoyl, —COOH, —$NR^4R^5$, —C(O)—$OR^3$, —C(O)—$NR^4R^5$, —$SO_2$—$OR^5$ or —$SO_2$—$NR^4R^5$, wherein $R^3$, $R^4$, and $R^5$ are independently hydrogen or $C_1$-$C_6$ alkyl;

n is 0, 1, 2, or 3;

$R^7$ is halogen, $C_1$-$C_6$ alkyl, $C_1$-$C_6$ haloalkyl, $C_1$-$C_6$ alkoxy, $C_1$-$C_6$ haloalkoxy, nitro, cyano, aryl, heteroaryl, heterocycloalkyl, $C_2$-$C_6$ alkanoyl, —COOH, —$NR^4R^5$, —C(O)—$OR^3$, —C(O)—$NR^4R^5$, —$SO_2$—$OR^5$ or —$SO_2$—$NR^4R^5$, wherein $R^3$, $R^4$, and $R^5$ are independently hydrogen or $C_1$-$C_6$ alkyl; and pharmaceutically acceptable salts thereof.

In an embodiment, the compound of Formula (II) is a compound of Formula (IIa), wherein $R^7$ is defined above.

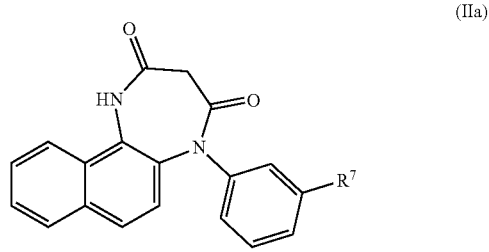
(IIa)

In an embodiment, $R^7$ of Formula (II) or (IIa) is heterocycloalkyl, specifically 1,2,4-oxadiazol-3-yl-5(4H)-thione or 1,2,4-oxadiazol-3-yl-5(4H)-one, and more specifically 1,2,4-oxadiazol-3-yl-5(4H)-thione.

A specific compound of Formula (II) is 5-[3-(5-thioxo-4H-[1,2,4]oxadiazol-3-yl)phenyl]-1H-naphtho[1,2-b][1,4]diazepine-2,4(3H,5H)-dione, having the formula or a pharmaceutically acceptable salt thereof.

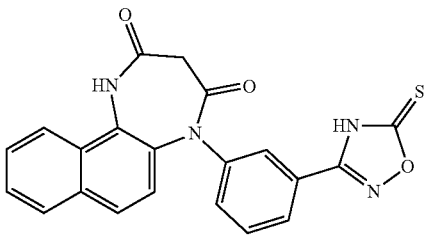 [SMILES: O=C1CC(=O)N(c2cccc(-c3noc(=S)[nH]3)c2)c2ccc3ccccc3c2N1]

In certain situations, the compounds of Formulae I, Ia, II, and IIa may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with double bonds may occur in Z- and E-forms, with all isomeric forms of the compounds being included in the present disclosure. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

In an embodiment, the stroke is an ischemic stroke. Ischemic stroke is defined herein as a stroke in which an artery to the brain is blocked. In another embodiment, the stroke is a hemorrhagic stroke or a TIA.

In an embodiment, the antagonist of the P2X4 receptor is administered during the acute phase of stroke, between the time the stroke occurs and lasting for up to about 7 days after stroke. In one embodiment, administration of the antagonist of the P2X4 receptor is ceased after the acute phase of stroke, after 7 days post-stroke. In another embodiment, the antagonist of the P2X4 receptor is administered in the acute, the subacute, the chronic phase of stroke, or a combination comprising at least one of the foregoing. Administration during the chronic phase of stroke is expected to be beneficial.

In an embodiment, administering the antagonist of the P2X4 receptor can be oral administration, for example, administration of a solid or liquid oral pharmaceutical formulation.

In another embodiment, administering the antagonist of the P2X4 receptor can be intravenous injection, such as injection into the general circulation or by targeted infusion whereby the agent is slowly supplied close to the site of the blockage that triggered the stroke. Infusion can be via an endovascular catheter such as a catheter ready to be used, being used, or having been used in providing a thrombolytic therapeutic to the subject; or a catheter having been used in conjunction with a procedure on the subject involving use of a clot-removal device.

The antagonist of the P2X4 receptor is administered a few minutes to up to 3 hours prior to administering a thrombolytic therapeutic or clot retrieval mechanically via an endovascular approach (also known as mechanical lysis) to the subject; wherein the antagonist of the P2X4 receptor is administered concomitantly with a thrombolytic therapeutic or clot retrieval mechanically via an endovascular approach to the subject; or wherein the antagonist of the P2X4 receptor is administered after a thrombolytic therapeutic or clot retrieval mechanically via an endovascular approach is administered to the subject.

Thrombolytic therapeutics include such as aspirin, clopidogrel, triclopidine, tissue plasminogen activator, urokinase, streptokinase, or a combination comprising at least one of the foregoing.

For oral administration, the pharmaceutical preparation can be in liquid form, for example, solutions, syrups or suspensions, or can be presented as a drug product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions can take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e. g., magnesium stearate, talc or silica); disintegrants (e.g., potato starch or sodium starch glycolate); or wetting agents (e.g., sodium lauryl sulphate). The tablets can be coated by methods well-known in the art.

Preparations for oral administration can be suitably formulated to give controlled release of the active compound.

For buccal administration, the compositions can take the form of tablets or lozenges formulated in conventional manner.

For administration by inhalation, the compositions are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compositions can be formulated for parenteral administration by injection, e.g., by bolus injection or continuous infusion via either intravenous, intraperitoneal or subcutaneous injection. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

In addition to the formulations described previously, the compositions can also be formulated as a depot preparation. Such long acting formulations can be administered by implantation (e.g., subcutaneously or intramuscularly) or by intramuscular injection. Thus, for example, the compositions can be formulated with suitable polymeric or hydrophobic materials (e.g., as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions can, if desired, be presented in a pack or dispenser device, which can contain one or more unit dosage forms containing the active ingredient. The pack can for example comprise metal or plastic foil, such as a blister pack. The pack or dispenser device can be accompanied by instructions for administration.

The amount of the antagonist of the P2X4 receptor that may be combined with pharmaceutically acceptable excipients to produce a single dosage form will vary depending upon the host treated and the particular mode of administration. The specific therapeutically effective amount for a particular patient will depend on a variety of factors including the activity of the specific compound employed, the age, body weight, general health, sex, diet, time of administration, route of administration, rate of excretion, drug combination, and the severity of the particular disease undergoing therapy. In some instances, dosage levels below the lower limit of the aforesaid range may be more than adequate, while in other cases still larger doses may be employed without causing any harmful side effects provided that such higher dose levels are first divided into several small doses for administration throughout the day. The concentrations of the compounds described herein found in therapeutic compositions will vary depending upon a number of factors, including the dosage of the drug to be administered, the chemical characteristics (e.g., hydrophobicity) of the compounds employed, and the route of administration. In an embodiment, the antagonist of the P2X4 receptor is administered at a dosage of about 0.05 mg/kg to about 0.5 mg/kg to about 5 mg/kg of body weight of the subject.

The invention is further illustrated by the following non-limiting examples.

EXAMPLES

Materials and Methods for Example 1—Methods

Mice: Global and MS P2X4R KO mice were maintained and bred at the University of Connecticut Health Center (Farmington Conn.). Details of the generation of global and MS Cre mice are provided below.

The P2X4 targeting vector was prepared by recombination as described in the art. Briefly, 15 kb of DNA containing the P2X4 intron 1 to 4 genomic sequence was retrieved from an RP23 bacterial artificial chromosome (BAC) obtained from the BACPAC Resources Center at the Children's Hospital Oakland Research Institute, Oakland, Calif. The first loxP site was inserted into intron 4 and the second loxP site together with the Frt-PGKneo-Frt cassette was inserted in intron 1 in the opposite direction. The final targeting vector was then electroporated into embryonic stem cells derived from an F1(129Sv/C57BL6j) blastocyst. F1 pups with P2X4 exon 2 to 4 floxed by loxP sites were obtained by breeding chimeric mice with ROSA26-Flpe mice (Jax stock no: 009086) to remove the PGKneo cassette, and subsequent breeding was maintained in the C57BL6/J background. These mice were then crossed with mice with the LysM Cre promoter specific for myeloid cells to generate global or MS P2X4R KO mice. In brief, MS P2X4R KO mice were achieved by crossing the loxP-flanked P2X4R mice (P2X4R flox/flox) with mice expressing Cre recombinase under the control of the murine M lysozyme promoter, which is specific for cells of the myeloid lineage (LysM Cre). Homozygous LysM Cre mice on a C57BL/6 background were purchased from Jackson Laboratory Harbor, Me.), and mated with the heterozygous P2X4R flox/+ animals, to generate heterozygous conditional KO mice with LysMcre (LysM Cre/P2X4Rflox/+). Heterozygous matings, LysMcre/P2X4Rflox/+ mice crossed with P2X4R flox/+ mice, were employed to generate MS P2X4R KO mice and their littermate control mice. Double floxed mice without LysM Cre (P2X4R flox/flox LysM Cre), mice with a WT allele but carrying LysM Cre (LysM Cre/P2X4R+/+), and WT mice with no Flox/flox or LysMCre were used as "WT" controls. Similarly, global P2X4R KO mice were generated by crossing P2X4R flox/flox and Hprt1 Cre mice as described in the art.

We confirmed deletion by Western blot analysis (data not shown). Weight-matched littermates were used as WT controls approximately 20-25 g (8-10 weeks old). A total of 63 global P2X4R KO and WT mice (both male and female) were randomly divided and subjected to stroke. In the final analysis, a total of 58 mice were included due to stroke-induced death of five male WT mice. We used a total of 109 MS P2X4R KO and WT mice (both males and females) for infarct and quantitative PCR (qPCR) analyses (acute outcome at day 3), out of which we used 103 mice in the final analyses due to the death of six mice (4 male and 2 female) after stroke. We used a total of 116 MS P2X4R KO and WT mice (both males and females) for biochemical and chronic behavioral analyses, out of which total 103 mice were used in the final analyses due to the death of 13 mice (8 male and 5 female) after stroke. The study was approved by the institutional animal care and use committee and the procedures were in accordance with institutional, National Institutes of Health, STAIR, and RIGOR guidelines.

Middle cerebral artery occlusion and bilateral ovariectomy: We induced focal transient cerebral ischemia by a 60-minute right middle cerebral artery occlusion (MCAo) under isoflurane anesthesia followed by reperfusion for either 3, 15, or 30 days. We selected the three-day outcome because the infarct matures completely and shows minimal variation in its volume by that time. The 15- and 30-day time points represent sub-acute and chronic recovery as discussed in the art. Briefly, we performed a midline ventral neck incision and unilateral right MCAo by advancing a 6.0 silicone rubber-coated monofilament (Doccol Corporation, CA) 10-11 mm from the internal carotid artery bifurcation via an external carotid artery stump. We monitored rectal temperatures with a temperature control system (Fine Science Tools, Canada), maintaining the temperature at approximately 37° C. during surgery with an automatic heating pad. We used laser doppler flowmetry (DRT 4/Moor Instruments Ltd, Devon, UK) to measure cerebral blood flow and to confirm occlusion (reduction to 15% of baseline cerebral blood flow) and reperfusion. All animals were fed with wet mash for one week after surgery to ensure adequate nutrition for chronic endpoints, as animals have rearing deficits after stroke. In sham mice, we performed identical surgeries except the suture was not advanced into the internal carotid artery. For the gonadal hormone-mediated outcome study, we ovariectomized (ovxed) female mice two weeks prior to stroke surgery.

We performed ovx in MS P2X4R KO WT littermates' mice approximately 2 weeks prior to stroke as described previously. Briefly, female mice were anesthetized with 4-5% inhaled isoflurane and maintained at 1-1.5% via face mask. A lateral retroperitoneal incision was made midway between the costal margin and iliac crest, parallel to the spine on both sides of skin. The muscle and fascia were gently retracted to expose the fallopian tube that follows anteriorly to the ovary. The ovarian artery and vein were ligated: the ovary was removed with the help of a cauterizer. The area was then irrigated with saline, the muscle was repaired with surgical nylon suture, and the skin was closed with wound staples. Following ovx, mice recovered for at least two weeks prior to stroke.

Neurological deficit score: The neurological deficit (ND) score is a crude assessment of post-stroke behavioral recovery. We recorded ND scores, ranging from 0 to 4, at several time points after stroke. Our standard scoring system was as follows: 0, no deficit; 1, forelimb weakness and torso turning to the ipsilateral side when held by the tail; 2, circling to affected side; 3, unable to bear weight on affected side; and 4, no spontaneous locomotor activity or barrel rolling.

Cresyl violet staining for infarct volume and tissue atrophy analysis: We measured tissue infarct (day 3) or tissue atrophy (day 30) after stroke as described in the art. Briefly, we sacrificed the mice after stroke surgery with an overdose of Avertin (250 mg/kg intraperitoneally, i.p). After blood collection by cardiac puncture, we performed trans-cardiac perfusion on the mice using cold phosphate buffered saline (PBS) followed by 4% paraformaldehyde. Brains were then fixed overnight and placed in cryoprotectant (30% sucrose in PBS) for 72 hours before processing. We then sliced the brains into 30-μm free-floating sections using a freezing microtome; every eighth slice was mounted and stained with cresyl violet. We then used these 30-μm sections for infarction, tissue atrophy calculations, and immunohistochemistry analysis as described in the art. An investigator blinded to the experimental cohort performed the data analyses.

Sensory motor deficit test: We used the open field test (OFT) and rotarod test to measure spontaneous locomotor activity/anxiety-like behavior and motor balance coordination, respectively, at baseline and post-mcao days 2, 7, 14, 21, and 28. As the OFT is a non-stressful test, we performed the OFT prior to the rotarod test, on the same day with one hour difference between tests.

Open field test: The OFT is a common measure of exploratory behavior and general activity in rodents, which can be used both qualitatively and quantitatively. Briefly, we placed mice in a corner of a clear acrylic box (16"×16") and allowed them to explore the box for ten minutes. We quantified locomotor activity as the total number of beam breaks by a computer-operated, open-field photobeam activity system (San Diego Instruments, San Diego, Calif.). We calculated the percentage of beam breaks in the center zone (16/3"×16/3") compared to the total as a measure of anxiety-like behavior. Importantly, OFT tests can be administered at several time points to view trends without hindrance by habituation.

Rotarod test: The rotarod test examines motor coordination in mice. We placed mice on a rotating cylindrical rod accelerating from two to ten rotations per minute, over a span of five minutes. Each subject performed two trials with a 20-minute break between the two trials. We recorded the latency to fall from the rotating rod for each trial (in seconds), and used the mean latency for comparison between groups.

Tail suspension test: We used the tail suspension test (TST) to assay depression-like phenotypes in mice, based on the premise that mice subjected to inescapable stress become immobile. We performed the TST as described previously. Briefly, we placed mice in the behavioral room for one hour prior to testing to allow acclimatization. We suspended mice individually by the tail on fixed rod using paper tape, 60 cm above the surface of the table. We recorded for six minutes using a digital video camera (JVC Everio, Victor Company, Japan). A trained observer who was blinded to the treatment conditions evaluated the duration of immobility. The mouse was considered immobile in the absence of initiated movement. Due to the potential stress induced by the TST, we performed this test only once prior to sacrifice, at day 29.

Sucrose consumption test: The sucrose consumption test (SCT) is a measure of anhedonia, a symptom of depressive behavior. We performed the SCT at pre-stroke day −3 and post-stroke days 15 and day 30 in separate cohorts as described previously with a minor modification where we gave pre-weighed sugar pellets rather than sucrose solution. Briefly, we gave a pre-weighted (5 g) sucrose pellet to individually housed mice for overnight consumption in place of their regular food pellet. Twelve hours later, we recorded the remaining amount of sugar and calculated the amount of sugar consumed overnight. The mice were returned to normal conditions in the morning.

Immunohistochemistry and Western blot analysis: We sacrificed mice with an overdose of Avertin (250 mg/kg i.p) and collected blood from the right ventricle. After quick perfusion with 1×PBS, we rapidly removed the brain, and then separated and homogenized the frontal cortical region (perilesional cortex) of the right (ischemic) hemisphere as described in the art. To determine the protein concentration, we used a bicinchoninic acid protein assay kit (Thermo Fisher Scientific Inc., Rockford, Ill.) and performed Western blot analysis. We loaded a total of 20 µg of protein into each well of 4% to 15% sodium dodecyl sulfate electrophoresis gels and transferred to polyvinylidene difluoride membranes. We determined P2X4R expression in the ischemic or non-ischemic brain by both Western blot analysis using an anti-P2X4R antibody (1:500; Preoteintech Rosemont, Ill.) and immunolabeling with a different anti-P2X4R antibody (1:200 Alomone Labs, Jerusalem Israel). To determine cell-specific location, we co-labeled with target proteins using either NeuN (1:500, Abcam Cambridge, Mass.) or IbA-1 (1:500, Abcam, Cambridge, Mass.) antibodies as described (12).

Flow sorting of microglia and monocytes: We collected and prepared tissue for flow sorting of microglia and monocytes as described in the art. We identified resident microglia as the CD45int CD11b+Ly6C− population and the bone marrow-derived monocytes as the CD45hiCD11b+Ly6C+ population. We used cell type-matched fluorescence minus one controls to determine the positivity of each antibody. To acquire data, we used an LSR II flow cytometer (BD Biosciences, Billerica, Mass.) with FACsDIVA 6.0 (BD Biosciences, Billerica, Mass.) and FlowJo (Treestar Inc. Ashland, Oreg.) software. For each antibody, we determined gating based on fluorescence minus one controls. We collected sorted microglia or monocytes in trizol for qPCR analysis.

Quantitative PCR: We isolated total RNA from either perilesional cortex or flow-sorted microglia/monocytes of MS P2X4R KO and WT littermate mice using the triazole method. We performed reverse transcription and qPCR as per instructions of the TaqMan® RNA reverse transcription kit (Ambion, Life Technologies, Camarillo, Calif.) and Taqman® universal master mix reagent (Ambion, Life Technologies, Camarillo, Calif.).

Enzyme-linked immunosorbent assay for IL-1β expression in plasma and tissue: Blood samples were collected prior to sacrifice the animal and spun at 6,000 g for ten minutes at 4° C.; collected plasma was stored at −80° C. until further use. We analyzed plasma samples (no dilution) and brain tissue homogenates (in HEPES lysis buffer) for IL-1β levels using an IL-1β (Mouse) enzyme-linked immunosorbent assay (ELISA) ready-set-go kit with a sensitivity: 8 pg/mL (eBioscience Thermofisher, Waltham, Mass.).

Statistics: Data from individual experiments are presented as mean±SEM and statistically evaluated by Student's t-test (for comparison between two experimental groups; WT vs. KO), by one-way or two-way with repeated measure (genotype and time as variables) analysis of variance (ANOVA) with a Bonferroni post hoc test to correct for multiple comparisons (GraphPad Prism Software Inc., San Diego, Calif.,). As the ND scores are ordinal in nature, we used the Mann-Whitney U test. We considered a probability value of $p<0.05$ to be statistically significant. An investigator blinded to the experimental groups performed the data analyses.

Example 1: P2X4R Expression Increases after Stroke

Three days after stroke, P2X4R expression increased in the perilesional cortical region of the ischemic hemisphere in male WT mice (FIG. 1A). Using co-localization studies, we found that the P2X4R expression was primarily on microglial cells (Iba1+; FIG. 1A, B) and to a lesser extent on neuronal cells (NeuN+, FIG. 1C). Confirming the immunohistochemistry data, Western blot analysis showed a progressive increase in P2X4R expression over the first three days after stroke as compared to sham (FIG. 1D).

Example 2: Global and MS P2X4R KO Show Changes in Microglial Morphology after Stroke In addition to the high expression of P2X4R in microglial cells, co-labeling with Iba-1 revealed an increase in microglial activation (based on morphological changes) in WT male mice after three days of stroke in the perilesional cortex of the ipsilateral hemisphere. While the WT mice showed an amoeboid or round morphology characteristic of a highly activated state, both the global and MS P2X4R KO mice showed shorter processes, less arborization, and larger soma, indicating an intermediate activation state (FIGS. 2A and B). These data suggest that P2X4Rs are involved in microglia/macrophage cell activation.

Example 3: Global P2X4R KO Mice Show Acute Neuroprotection

We next examined post-stroke recovery at an acute time point after stroke (day 3). We found that both male and female P2X4R global KO mice showed significant neuroprotection at this time point. Specifically, male mice showed a reduction in cortical, striatal, and total hemispheric infarct volume compared to WT littermates (FIG. 3A); female mice displayed a similar reduction in cortical and total hemispheric infarct volume but not in striatal infarct volume (FIG. 3B). Behaviorally, both sexes showed improvements in the ND score compared to control mice (FIG. 3C, D), indicating acute post-stroke behavioral benefits. In contrast to the acute time point, we did not see any changes in tissue atrophy (FIG. 3E) or ND scores (FIG. 3F) between male or female global KO and WT mice at a chronic stage of stroke (day 30), suggesting that the acute benefits in the KO mice were lost during progressive recovery.

Example 4: MS P2X4R KO Mice Show Acute Neuroprotection in Female Mice after Stroke Given that the majority of P2X4Rs are expressed in the brain on myeloid cells (microglia, monocytes, and macrophages), we next examined the effects of stroke in mice lacking P2X4R specifically in myeloid cells. Three days after stroke, MS P2X4R KO and WT male mice showed no change in hemispheric, striatal, or cortical infarct volume (FIG. 4A). However, female KO mice showed a significant reduction in cortical and total hemispheric infarct volume and a trend for a reduction in striatal infarct volume (68.23±1.5 vs. 56.3±7.0, p=0.1 vs WT) (FIG. 4B). To probe the role of the ovarian sex hormone estrogen in this effect, we ovxed MS P2X4R KO female mice two weeks prior to stroke surgery; these showed the same level of neuroprotection in terms of striatal, cortical and hemispheric infarct volume change as non-ovxed mice (FIG. 4C). Thus, acute estrogen does not appear to contribute to the P2X4R effect. At a chronic time point (day 30), we did not observe differences in tissue atrophy between male or female MS P2X4R KO versus WT mice (data not shown). We next assessed behavioral recovery in the MS P2X4R KO mice, and observed no change in ND score in male or female (ovxed or non-ovxed) KO mice three days after stroke compared to WT littermates (FIGS. 4D,-F). However, female MS P2X4R KO mice showed complete recovery by day 14 in ND score (FIG. 5A), unlike WT controls or male P2X4R KO mice.

Example 5: Effect of MS P2X4R Deletion on Sensorimotor Function During Chronic Recovery after Stroke Next, we examined the role of MS P2X4R in more complex behavioral outcomes after stroke. At baseline, we found no differences between the genotypes for either of the behavioral tests we examined (i.e., OFT and rotarod test; data not shown). After ischemic stroke, MS P2X4R deletion did not affect total exploratory behavior in the OFT at any time point for either gender (FIG. 5B). However, male (but not female) MS P2X4R KO mice showed swift recovery of an anxiety-like behavior in the OFT at an acute time point (FIG. 5C). In the rotarod test, both male and female MS P2X4R KO mice were more resistant to the loss of grip strength during the acute period of ischemia/reperfusion injury (FIG. 5D). However, these differences diminished within two weeks of recovery.

Example 6: MS P2X4R KO Mice Show a Depressive-Like Behavioral Phenotype

Given that loss of P2X4R leads to a reduction in BDNF, which is linked to depression, we performed tests for depressive-like behaviors (anhedonia and lack of motivation). At baseline, male and female MS P2X4R KO mice showed no difference in anhedonia (based on the SCT) compared to WT littermates (FIG. 6A); however, after stroke both genders showed reduced consumption of sucrose at a sub-acute (day 15) and chronic (day 30) time point (FIG. 6B,C). Consistent with the SCT results, MS P2X4R KO mice of both genders showed an increased duration of immobility (i.e., loss of escape behavior/lack of motivation to rescue itself) in the TST measured at day 29 after stroke (FIG. 6D). These data suggest that the absence of P2X4Rs on microglia/macrophages induces depression-like behavior after stroke.

Example 7: MS P2X4R KO Mice Show Increased Tissue mRNA Levels of Pro-Inflammatory Cytokines and Decreased Depression-Related Gene Expression after Stroke Pro-inflammatory cytokines, neurotrophins (e.g., BDNF), neuronal cell adhesion molecules, and serotonergic pathway genes have a well-established role in depression. Thus, we analyzed the expression levels of these genes using qPCR analysis on brain tissue from MS P2X4R KO mice at 3 and 30 days after stroke. Male and female KO mice showed a significant increase in the mRNAs for the pro-inflammatory cytokines IL-6, IL-1β, and TNF-α compared to WT (FIG. 7A-C) except for IL-6 levels at day 30. Without being held to theory, we hypothesized that these elevated levels of cytokine transcripts were contributed primarily by myeloid cells. To test this, we sorted microglia and monocytes by flow cytometry and analyzed mRNA isolated from these cells. As anticipated, MS P2X4R KO mice showed elevated levels of intracellular cytokine mRNA in both microglia (days 3 and 30; FIG. 8A,B) and monocytes (day 3; FIG. 8C) isolated from KO mice as compared to WT mice. We could not detect these cytokines in monocytes collected at 30 days of stroke due the very low numbers of monocytes (few hundreds of cells/mouse tissue; data not shown). These observations suggest that MS P2X4Rs might be involved either in the release or maturation of inflammatory cytokines after stroke. Expression analysis of several important depression-related genes such as BDNF, synaptophysin (syp), neural cell adhesion molecule (NCAM) 1, and 5-hydroxytryptamine (serotonin) receptor 2C (HTR2c) and HTR1a revealed a trend or a significantly reduced levels in KO mice brain tissue of both male and female animals (FIG. 9). We did not observe any change in depressive gene at the acute time point (data not shown). This observation suggests a putative interaction between P2X4R and genes pertinent to depressive behaviors.

Example 8: MS P2X4R KO Mice Show Reduced Pro-Inflammatory Cytokine IL-1β in Plasma To further confirm our hypothesis that KO mice show reduced release of matured cytokines, we performed an ELISA on a highly modulated cytokine, IL-1β. At the acute time point, total plasma levels of IL-1β cytokine were significantly lower in KO mice as compared to WT mice; however, we did not observe any change at day 30 (FIG. 10A). We did not observe a difference in brain tissue protein levels of IL-1β between WT and KO mice at any time point (FIG. 10B). The microglial protein level of IL-1β may be different in KO vs. WT mice; however, this potential difference could not be measured due to the low amount of proteins available from isolated microglia. Nevertheless, the overall data are consistent with the hypothesis that the P2X4R might plays an important role in stimulating the release of IL-1β from myeloid cells during acute ischemic insults.

Discussion of Examples 1-8

In this study, we performed both acute and chronic survival experiments to explore the therapeutic potential of P2X4R loss. We first found that P2X4Rs are expressed robustly on microglial cells following stroke. Consistent with this finding, microglial cells show increased proliferation 2-3 days following stroke, which coincides with the peak upregulation of microglial P2X4R expression. Microglia and peripheral macrophages/monocytes (i.e., myeloid cells) are the principal producers of inflammatory cytokines after ischemic stroke. Moreover, P2X4R-mediated activation of myeloid cells has been shown to contribute to neuroinflammation by releasing pro-inflammatory cytokines such as TNF-α and IL-1β. However, these studies either were performed in primary microglial cell culture, which is not physiologically relevant to stroke pathology in vivo, or used a pharmacological antagonist of P2X4R that can non-specifically block other P2XRs or block P2X4Rs on multiple cell types in the brain. Therefore, in this study, we took advantage of the Cre/LoxP system to generate MS P2X4R KO mice to investigate the role of myeloid P2X4R in stroke injury.

We saw an equal degree of neuroprotection in male and female global P2X4R KO mice compared to WT controls, likely due to an inhibition of release of pro-inflammatory cytokines like IL-1β and TNF-α and a subsequent blockade of inflammasome activation in the absence of P2X4R. The lack of a difference in tissue atrophy after 30 days suggests a possible reversal of the early benefits of loss of P2X4R during chronic recovery due to the absence of physiological functions of P2X4R in KO mice. However, when we assessed MS P2X4R KO mice, only females showed neuroprotection, suggesting a sex difference in the P2X4R response after stroke. This finding is consistent with recent findings that microglia responses may be sexually dimorphic. In these studies, the divergence between the male and female signaling pathways seemed to occur at the level of P2X4R with its upregulation in male mice only. However, other genes associated with microglial reactivity were shown to be upregulated in both sexes; therefore, perhaps P2X4R present on brain cells other than microglia neutralized the P2X4R-mediated acute neuroprotection in the males. Sex differences in stroke have been largely attributed to neuroprotection due to the activational effects of gonadal hormones such as estrogen. However, we observed a similar degree of neuroprotection in both ovxed and intact MS P2X4R KO mice, suggesting that the protection we observed was not related to the acute activational effects of estrogen. It is possible that sex chromosomes or organizational effects of steroids play a role early in development in this sexually dimorphic response which remains to be explored. Without being held to theory, the absence of chronic effects of global or MS P2X4R on tissue atrophy suggest that the acute benefits may have been counterbalanced by the chronic loss of the beneficial effect of P2X4R during recovery.

We next conducted mRNA gene expression profiles on several genes that are central to the neuroinflammatory response in cerebral ischemia (i.e., IL-1β, TNFα, and IL-6) both at day 3 and day 30 after stroke. We found consistently elevated levels of IL-6, IL-1β, and TNF-α mRNA in the brain of post-stroke MS P2X4R KO mice of both sexes as compared to WT mice, irrespective of infarct size. Moreover, we found a reciprocal relationship in expression between these cytokines and other depression-related gene levels in MS KO mice. The increased cytokine gene expression levels in the KO mice appears to be in conflict with prior work, where P2X4R activation has been shown to increase inflammation. However, these paradoxical findings may be explained by the notion that an activated microglia signal for increased pro-inflammatory cytokine mRNA expression is not associated with release of cytokines from cells due to an absence of P2X4R in KO mice. Our cytokine expression data from flow-sorted microglia revealed elevated mRNA levels of IL-1β and TNF-α both at early and delayed time points after ischemic stroke are consistent with this concept. Thus, these KO mice may show protection from damage as a result of reduced release of pro-inflammatory cytokines at an early time point. The fact that the IL-1β protein level was not changed in the brain tissues but was reduced in plasma of KO vs. WT mice at day 3 after stroke point to reduced extracellular cytokines as a potential protective mechanism.

Despite the detrimental effect of early activation of P2X4Rs, these receptors are involved in the release of BDNF; thus they may modulate chronic recovery after stroke. We and several other laboratories have correlated the chronic loss of BDNF with poor behavioral recovery and depressive behaviors at chronic time points after ischemic injury. Furthermore, infarct size measurements alone can be misleading and P2X4Rs may also modulate social behavioral responses. Therefore, we extended our study to ascertain the chronic behavioral effects of loss of MS P2X4R after stroke. We did not observe a change in tissue atrophy measured 30 days after stroke in MS P2X4R KO mice in either sexes, mirroring our finding with global KO mice. However, we found that MS ablation of P2X4Rs resulted in a range of abnormal behavioral phenotypes in both male and female mice. The acute recovery seen in the rotarod test and in anxiety-like behaviors that we observed in MS P2X4R KO might correspond to a reduced surge in inflammatory cytokines activity as a result of impaired release; however, during chronic survival these benefits were lost either due to an overall reduction in post-stroke inflammation or an absence of a beneficial effect of P2X4R such as the lack of BDNF. Interestingly, both male and female displayed depression-like behavior as measured by the TST and SCT; these effects were independent of infarct size difference. The depression-like behaviors in MS P2X4R KO mice suggest an important role of microglial P2X4R in chronic post-stroke recovery, likely mediated by BDNF release.

Prior studies suggest that cytokines such as IL-1β, IL-6, and TNF-α are associated with depressive behaviors both pre-clinically and clinically. However, other reports contradict this notion by suggesting that depressive behaviors might be unrelated to the pro-inflammatory actions of these cytokines. These cytokines also reduce BDNF release or interrupt its binding to the trk-B receptor and thus might further potentiate depressive behaviors. In addition to reduced BDNF in MS P2X4R KO mice, other possible causes of the depression-like behaviors in the KO mice may be related to reduced expression of NCAM1 and syp in mice, as genetic deletion of NCAM leads to depressive-like behaviors and reduced expression of syp was reversed by antidepressant drugs. The serotonergic system has also been widely implicated in major depressive disorder (MDD) in both clinical and preclinical research. The role of the serotonin transporter in MDD has been highlighted in genes by environment association studies. In addition, the serotonin transporter is a critical player in the mechanism of most effective antidepressant treatments, selective serotonin reuptake inhibitors. While the majority of the 15 known receptors for serotonin have been implicated in depression or depressive-like behaviors, the serotonin HTR 1A, 1B, and 2C receptors are amongst the most important and studied. Our data provide preliminary evidence that P2X4R is somehow involved in microglial-mediated depressive behavior after stroke. However, a detailed study is needed to dissect the direct downstream targets of P2X4R that lead to depressive behavior.

Example 9: Effect of 5 BDBD on Infarct Volume in WT Mice Model: Middle Cerebral Artery Occlusion Male C57B/6 (2-3 month old; 22-28 g) mice were used in this experiment. The ischemia duration was 60 minutes, with reperfusion for 72 hours. 5-BDBD- (0.5 mg/kg p.o./day in 1% DMSO and 0.5% methyl cellulose suspension) was administered for 3 days. The first dose was given at 4 hour after stroke. The vehicle was 1% DMSO in 0.5% methyl cellulose suspension. Staining was done with cresyl violet. As shown in FIGS. 11 and 12, 5-BDBD reduces cortical and hemispheric infarct volume and Neurological deficit score measured after 3 days of stroke.

Example 10: Effect of 5 BDBD on Chronic Behavioral Recovery after Stroke

Male C57B/6 (2-3 month old; 22-28 g) mice were used in a Middle Cerebral Artery occlusion (MCAo) model. The ischemia duration was 60 mins and the reperfusion was 30 days. The drug was 5-BDBD- (0.5 mg/kg p.o./day in 1% DMSO and 0.5% methyl cellulose suspension) administered for 3 days. The first dose was given at 4 hour after stroke. Vehicle was 1% DMSO in 0.5% methyl cellulose (n=5 Behaviors were measured weekly using methods described above. (n=7).

Figure 13:
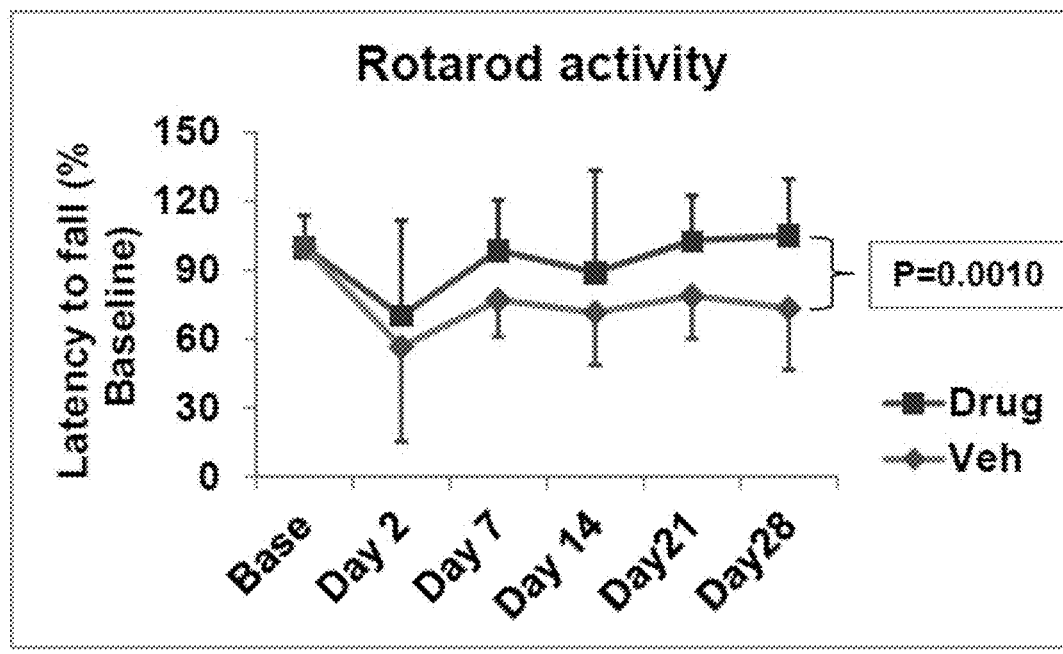
FIG. 13 shows a rotarod test (test for sensorimotor deficit) suggests overall significant difference between drug (5-BDBD) and vehicle treated mice.
Figure 14:
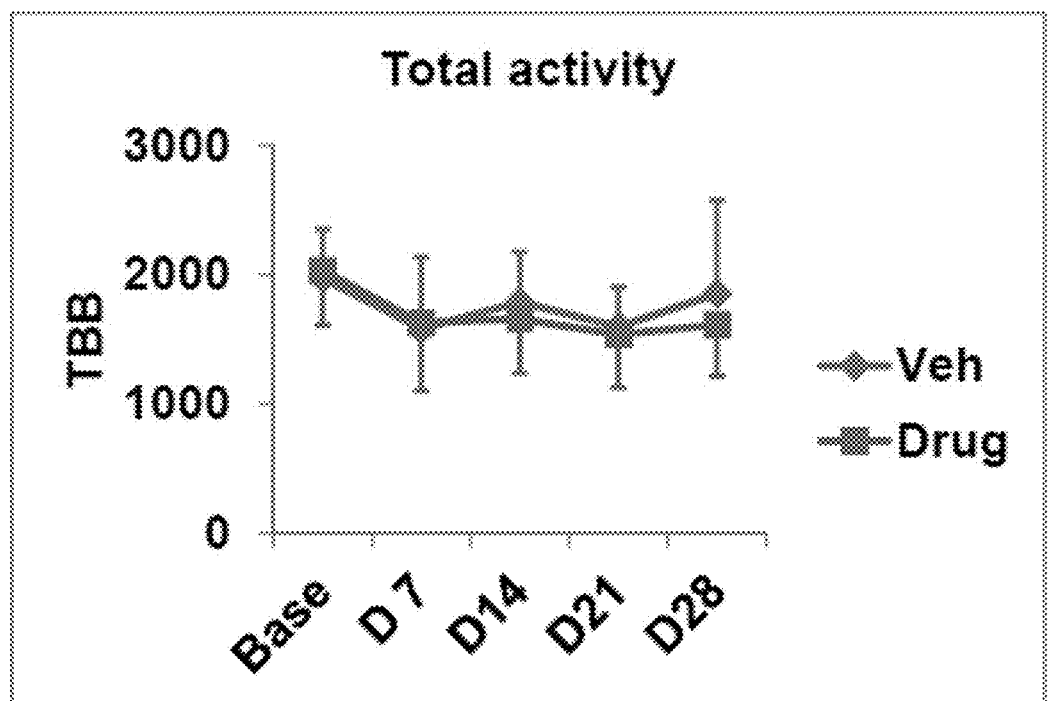
FIG. 14 shows total exploratory activity was similar in drug (5-BDBD) and vehicle treated mice.
Figure 15:
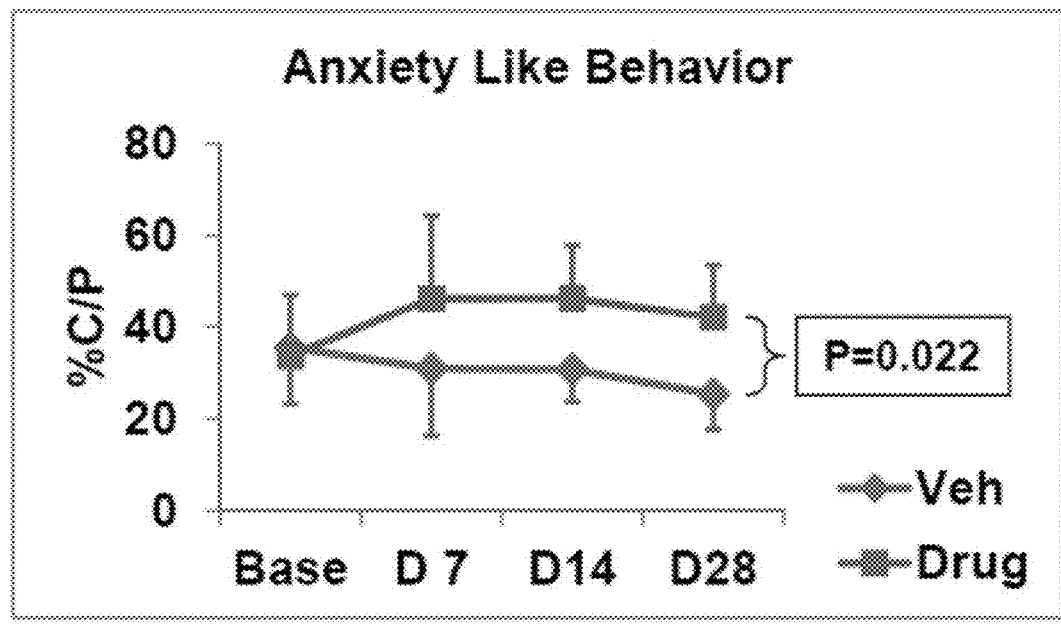
FIG. 15 shows that BDBD acute treatment reduces post stroke anxiety up to a month. (% C/P=% time spent in center/time spent in periphery).

As shown in FIG. 13, a rotarod test (test for sensorimotor deficit) suggests overall significant difference between drug (5-BDBD) and vehicle treated mice. FIG. 14 shows total exploratory activity was similar in drug (5-BDBD) and vehicle treated mice. FIG. 15 shows that BDBD acute treatment reduces post stroke anxiety up to a month. (% C/P=% time spent in center/time spent in periphery).

Example 11: Effect of NP1815PX (Water/PBS Soluble) on Infarct Volume after Stroke Injury Male C57/B (2-3 month old; 22-28 g) mice were used in a Middle Cerebral Artery occlusion (MCAo) model. The ischemia duration was 60 mins and the reperfusion was 72 hours. The drug was NP 1815 PX; (0.5-5 mg/kg) dissolved in 1×PBS and given as Alzet mini osmotic pump for 3 days with a release rate of 1 ul/hr. The pump was implanted immediately after reperfusion and starts to release drug after reaching equilibrium, usually 3-4 hours after implantation. The method of staining was TTC. The number of animals was Veh=7, Drug (0.5 mg/kg)=6, Drug (1.5 mg/kg)=6, Drug (5 mg/kg)=5.

Figure 16:
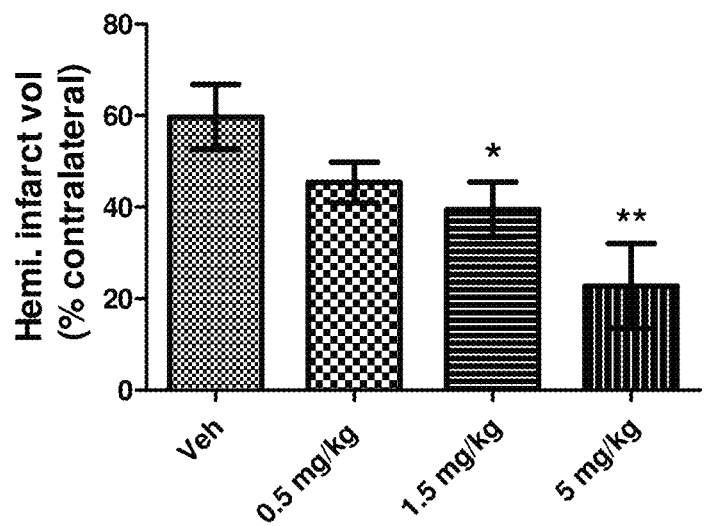
FIG. 16 shows the effect of increasing doses of NP-1815-PX on total ipsilateral hemispheric infarct volume after 3 days of stroke in mice. The number of animals in each group was 6-7. * and ** indicate a significant difference from vehicle treatment (Veh) at P<0.05 and P<0.01 respectively (ANOVA with Newman-Keuls post-hoc analysis).
Figure 17:
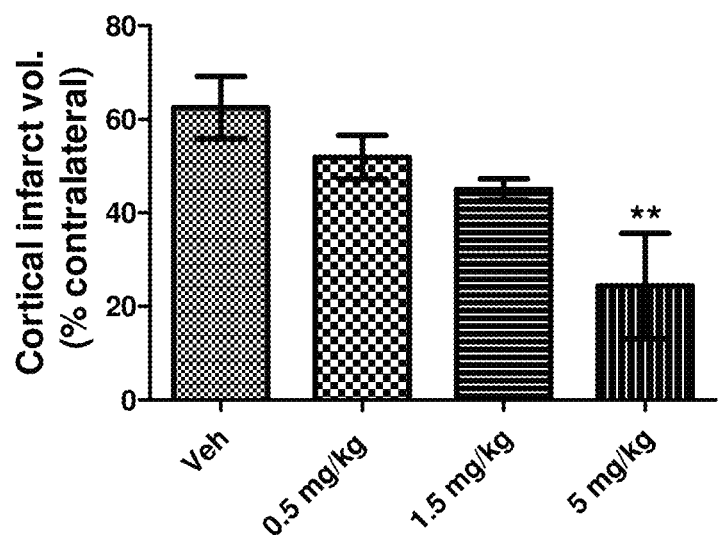
FIG. 17 shows the effect of increasing doses of NP-1815-PX on cortical infarct volume after 3 days of stroke in mice. The number of animals in each group was 6-7. ** indicates a significant difference from vehicle treatment (Veh) at P<0.01 (ANOVA with Newman-Keuls post-hoc analysis).
Figure 18:
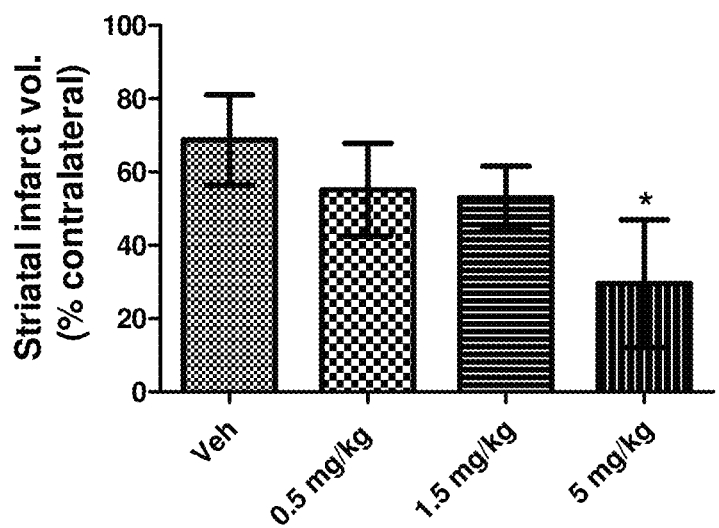
FIG. 18 shows the effect of increasing doses of NP-1815-PX on striatal infarct volume after 3 days of stroke in mice. The number of animals in each group was 6-7. * indicates a significant difference from vehicle treatment (Veh) at P<0.05 (ANOVA with Newman-Keuls post-hoc analysis).
Figure 19:
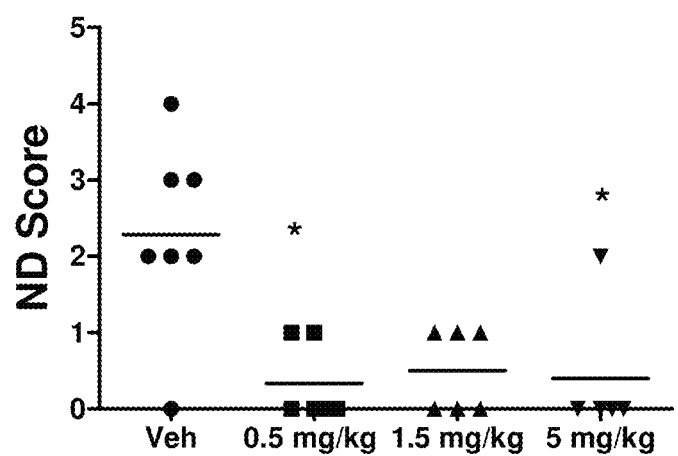
FIG. 19 shows the effects of increasing doses of NP-1815-PX on neurological deficit (ND) score in mice after 3 days of stroke. The number of animals in each group was 6-7. * indicates a significant difference from vehicle treatment (Veh) at P<0.05 and P<0.01 respectively (Nonparametric ANOVA using Kruskal-Wallis test followed by Dunn's multiple comparison test).

FIG. 16 shows the effect of increasing doses of NP-1815-PX on total ipsilateral hemispheric infarct volume after 3 days of stroke in mice. The number of animals in each group was 6-7. * and  indicate a significant difference from vehicle treatment (Veh) at $P<0.05$ and $P<0.01$ respectively (ANOVA with Newman-Keuls post-hoc analysis). FIG. 17 shows the effect of increasing doses of NP-1815-PX on cortical infarct volume after 3 days of stroke in mice. The number of animals in each group was 6-7.  indicate a significant difference from vehicle treatment (Veh) at $P<0.01$ (ANOVA with Newman-Keuls post-hoc analysis). FIG. 18 shows the effect of increasing doses of NP-1815-PX on striatal infarct volume after 3 days of stroke in mice. The number of animals in each group was 6-7. * indicates a significant difference from vehicle treatment (Veh) at $P<0.05$ (ANOVA with Newman-Keuls post-hoc analysis). FIG. 19 shows the effects of increasing doses of NP-1815-PX on neurological deficit (ND) score in mice after 3 days of stroke. The number of animals in each group was 6-7. * indicates a significant difference from vehicle treatment (Veh) at $P<0.05$ and $P<0.01$ respectively (Nonparametric ANOVA using Kruskal-Wallis test followed by Dunn's multiple comparison test).

Based on data summarized in FIGS. 16-19, we conclude that a P2X4 antagonist, that is NP-1815-PX, with a structure different from that of 5-BDBD could reduce stroke infarct size and improve ND score when the drug was administered systemically via SC route during the acute phase of stroke.

ABBREVIATIONS AND TERMS USED

5-BDBD=5-(3-Bromophenyl)-1,3-dihydro-2H-Benzofuro[3,2-e]-1,4-diazepin-2-one
ANOVA=analysis of varience
BDNF=Brain Derived Neurotrophic Factor
ND=neurological deficit
OFT=open field test
NORT=novel object recognition task
P2X4R=P2X4 Receptor, also sometimes designated as P2X4 Receptor
P2X4R KO mice=P2X4 Receptor Knock out mice
TST=tail suspension test
Acute phase=the time period starting at the time a subject has a stroke and lasting from the time of stroke to day 7 after stroke. In humans, the acute phase is somewhat variable, but generally, human subjects are hospitalized during the acute phase of stroke.
Subacute phase=the time period from 7 days to about 3 months after a subject has a stroke. This is the phase in which human subjects experience the most recovery.
Chronic phase=the time period comprising about 3 months after stroke to end of life. In humans, substantial progress can be made during the chronic phase of stroke.
The term "substituted", as used herein, means that any one or more hydrogens on the designated atom or group is replaced with a selection from the indicated group, provided that the designated atom's normal valence is not exceeded. When a substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent. For example, —COOH is attached through the carbon atom.

As used herein, "alkyl" is intended to include both branched and straight-chain saturated aliphatic hydrocarbon groups, having the specified number of carbon atoms. Thus, the term $C_1$-$C_6$ alkyl as used herein includes alkyl groups having from 1 to about 6 carbon atoms. When $C_0$-$C_n$ alkyl is used herein in conjunction with another group, for example, phenyl$C_0$-$C_4$ alkyl, the indicated group, in this case phenyl, is either directly bound by a single covalent bond ($C_0$), or attached by an alkyl chain having the specified number of carbon atoms, in this case from 1 to about 2 carbon atoms. Examples of alkyl include, but are not limited to, methyl, ethyl, n-propyl, isopropyl, n-butyl, t-butyl, n-pentyl, and sec-pentyl.

"Alkoxy" represents an alkyl group as defined above with the indicated number of carbon atoms attached through an oxygen bridge. Examples of alkoxy include, but are not limited to, methoxy, ethoxy, n-propoxy, propoxy, n-butoxy, 2-butoxy, t-butoxy, n-pentoxy, 2-pentoxy, 3-pentoxy, iso-pentoxy, neopentoxy, n-hexoxy, 2-hexoxy, 3-hexoxy, and 3-methylpentoxy.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

As used herein, the term "aryl" indicates aromatic groups containing only carbon in the aromatic ring or rings. Such aromatic groups may be further substituted with carbon or non-carbon atoms or groups. Typical aryl groups contain 1 to 3 separate, fused, or pendant rings and from 6 to about 18 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

In the term "(aryl)alkyl", aryl and alkyl are as defined above, and the point of attachment is on the alkyl group. This term encompasses, but is not limited to, benzyl, phenylethyl, and piperonyl. Likewise, in the term (aryl)carbhydryl, aryl and carbhydryl are as defined above and the point of attachment is on the carbhydryl group, for example a phenylpropen-1-yl group.

"Carbhydryl" as used herein, includes both branched and straight-chain hydrocarbon groups, which are saturated or unsaturated, having the specified number of carbon atoms.

"Cycloalkyl" as used herein, indicates saturated hydrocarbon ring groups, having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norbornane or adamantane.

"Haloalkyl" indicates both branched and straight-chain saturated aliphatic hydrocarbon groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge.

"Halo" or "halogen" as used herein refers to fluoro, chloro, bromo, or iodo.

As used herein, "heteroaryl" indicates a stable 5- to 7-membered monocyclic or 7- to 10-membered bicyclic heterocyclic ring which contains at least 1 aromatic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, and 5,6,7,8-tetrahydroisoquinoline. In the term "heteroarylalkyl," heteroaryl and alkyl are as defined above, and the point of attachment is on the alkyl group. This term encompasses, but is not limited to, pyridylmethyl, thiophenylmethyl, and pyrrolyl(1-ethyl).

The term "heterocycloalkyl" is used to indicate saturated cyclic groups containing from 1 to about 3 heteroatoms chosen from N, O, and S, with remaining ring atoms being carbon. Heterocycloalkyl groups have from 3 to about 8 ring atoms, and more typically have from 5 to 7 ring atoms. A $C_2$-$C_7$heterocycloalkyl group contains from 2 to about 7 carbon ring atoms and at least one ring atom chosen from N, O, and S. Examples of heterocycloalkyl groups include morpholinyl, piperazinyl, piperidinyl, pyrrolidinyl, 1,2,4-oxadiazol-3-yl-5(4H)-thione, and 1,2,4-oxadiazol-3-yl-5(4H)-one groups.

"Pharmaceutically acceptable salts" includes derivatives of the disclosed compounds wherein the parent compound is modified by making an acid or base salt thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional salts and the quaternary ammonium salts of the parent compound formed, for example, from inorganic or organic acids. For example, conventional acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method for treatment of a human subject who has had a stroke, the method comprising administering to the subject a pharmaceutical composition comprising an antagonist of the P2X4 receptor, wherein the antagonist of the P2X4 receptor is a compound of Formula (II)

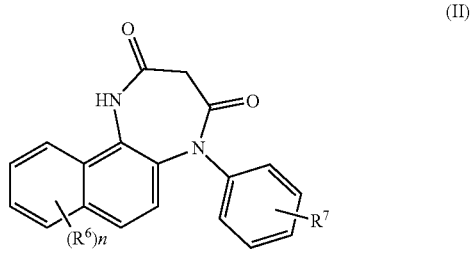

(II)

wherein $R^6$ is hydrogen, halogen, $C_1$-$C_6$ alkyl, $C_1$-$C_6$ haloalkyl, $C_1$-$C_6$ alkoxy, $C_1$-$C_6$ haloalkoxy, nitro, cyano, aryl, heteroaryl, heterocycloalkyl, $C_2$-$C_6$ alkanoyl, —COOH, —NR$^4$R$^5$, —C(O)—OR$^3$, —C(O)—NR$^4$R$^5$, —SO$_2$—OR$^5$ or —SO$_2$—NR$^4$R$^5$, wherein $R^3$, $R^4$, and $R^5$ are independently hydrogen or $C_1$-$C_6$ alkyl;

n is 0, 1, 2, or 3;

$R^7$ is halogen, $C_1$-$C_6$ alkyl, $C_1$-$C_6$ haloalkyl, $C_1$-$C_6$ alkoxy, $C_1$-$C_6$ haloalkoxy, nitro, cyano, aryl, heteroaryl, heterocycloalkyl, $C_2$-$C_6$ alkanoyl, —COOH, —NR$^4$R$^5$, —C(O)—OR$^3$, —C(O)—NR$^4$R$^5$, —SO$_2$—OR$^5$ or —SO$_2$—NR$^4$R$^5$, wherein $R^3$, $R^4$, and $R^5$ are independently hydrogen or $C_1$-$C_6$ alkyl; or a pharmaceutically acceptable salt thereof, and wherein the antagonist of the P2X4 receptor is administered during the acute phase of stoke, wherein the acute phase of stroke starts at the time the stroke occurs and lasting for 7 days.

2. The method of claim 1, wherein the compound of Formula (II) is a compound of Formula (IIa)

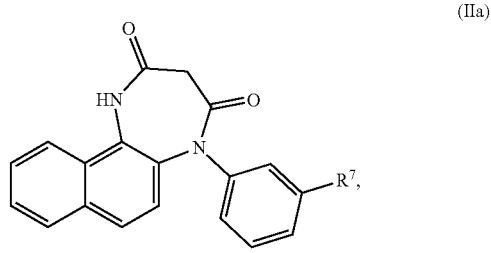

(IIa)

wherein $R^7$ is as defined in claim 1.

3. The method of claim 1, wherein $R^7$ is 1,2,4-oxadiazol-3-yl-5(4H)-thione or 1,2,4-oxadiazol-3-yl-5(4H)-one.

4. The method of claim 1, wherein the compound of Formula (II) is 5-[3-(5-thioxo-4H-[1,2,4]oxadiazol-3-yl) phenyl]-1H-naphtho[1,2-b][1,4]diazepine-2,4(3H,5H)-dione, or a pharmaceutically acceptable salt thereof.

5. The method of claim 1, wherein the stroke is an ischemic stroke.

6. The method of claim 1, wherein the administration of the antagonist of the P2X4 receptor is ceased after the day 7.

7. The method of claim 1, wherein the administration of the antagonist of the P2X4 receptor is continued through the subacute and/or the chronic phase of stroke.

8. The method of claim 1, wherein the administering the antagonist of the P2X4 receptor is by oral administration or intravenous injection.

9. The method of claim 8, wherein intravenous injection is injection into the general circulation, or targeted infusion whereby the antagonist of the P2X4 receptor is supplied close to the site of the blockage that triggered the stroke.

10. The method of claim 9, wherein the infusion is provided an endovascular catheter.

11. The method of claim 10, wherein the endovascular catheter has been previously used to provide a thrombolytic therapeutic agent to the subject.

12. The method of claim 10, wherein the endovascular catheter has been previously used in conjunction with a procedure on the subject involving a clot-removal device.

13. The method of claim 1, wherein the antagonist of the P2X4 receptor is administered a few minutes to up to 3 hours prior to administering a thrombolytic therapeutic or clot-removal device to the subject; wherein the antagonist of the P2X4 receptor is administered concomitantly with a thrombolytic therapeutic or clot-removal device to the subject; or wherein the antagonist of the P2X4 receptor is administered after a thrombolytic therapeutic or clot-removal device is administered to the subject.

14. The method of claim 1, wherein antagonist of the P2X4 receptor is administered at a dosage of about 0.05 mg/kg to about 0.5 mg/kg to about 5 mg/kg of body weight of the subject.

* * * * *